United States Patent [19]

Sainsbury et al.

[11] Patent Number: 5,516,788

[45] Date of Patent: May 14, 1996

[54] TETRAHYDROINDENOINDOLE COMPOUNDS USEFUL IN THE TREATMENT OF CONDITIONS ASSOCIATED WITH FREE RADICAL FORMATION

[75] Inventors: Malcolm Sainsbury, Bristol, United Kingdom; Howard G. Shertzer, Cincinnati, Ohio

[73] Assignees: University of Bath, Bath, United Kingdom; University of Cincinnati, School of Medicine, Cincinnati, Ohio

[21] Appl. No.: 369,874

[22] Filed: Jan. 6, 1995

Related U.S. Application Data

[63] Continuation of Ser. No. 776,658, Oct. 15, 1991, abandoned, which is a continuation-in-part of Ser. No. 709,660, Jun. 3, 1991, abandoned, which is a continuation of Ser. No. 542,511, Jun. 22, 1990, abandoned.

[30] Foreign Application Priority Data

Jun. 22, 1989 [SE] Sweden .................................. 8902274
Oct. 16, 1990 [GB] United Kingdom ................... 9022453
Dec. 21, 1990 [GB] United Kingdom ................... 9027895

[51] Int. Cl.⁶ ..................... C07D 209/70; C07D 209/94; A61K 31/40
[52] U.S. Cl. ........................................... 514/410; 548/420
[58] Field of Search ............................ 548/420; 514/410

[56] References Cited

PUBLICATIONS

Eisch, et al., Tetrahedron Letters 20, pp. 1647–1650, (1976).
Horrocks, et al., J. Chem Phys. 47, pp. 3241–3247, (1967).
Horrocks, et al., J. Chem. Phys. 49, pp. 2907–2912, (1968).
Horrocks, et al., J. Chem. Phys. 49, pp. 2913–2917 (1968).
Kempter, et al., J. Prakt. Chem. 18, pp. 39–46, (1962).
Kempter, et al., Chem. Abstracts 57, p. 15052, (1962).
Kempter et al., Chem. Abstracts, 7th Collective Subject Index, p. 11655, (1969).
Letcher, et al., J. Chem. Soc. Chem. Commun., pp. 1602–1603 (1987).
Bill, et al., Heterocycles 20, pp. 2433–2436, (1983).
Bill, et al., Chem. Abstracts 100, No. 191091W, (1984).
Buu–Hoi, et al., J. Chem. Soc. 2, pp. 2225–2228, (1952).
Seka, et al., Ber. Deutsch. Chem. Gef. 75B, pp. 1730–1738, (1942).
Beilsteins Handbuch Der Organischen Chemie 20, pp. 310–311, (1953).
Anastassiou, et al., J. Chem. Soc. Chem. Commun., pp. 647–648, (1981).
Schertzer, et al., Fd. Chem. Toxic. 26, pp. 517–522, (1988).
Schertzer, et al., FASEB Journal 2, p. A407, No. 648, (1988).
Schertzer, et al., Chem. Abstracts 109, p. 248, No. 224224h, (1988).
Leuchs, *Annalen Der Chemie*, 461, pp. 27–46, 1928.

*Primary Examiner*—Joseph Paul Brust
*Attorney, Agent, or Firm*—White & Case

[57] ABSTRACT

The invention concerns compounds and their enantiomers of the formula IA or IB

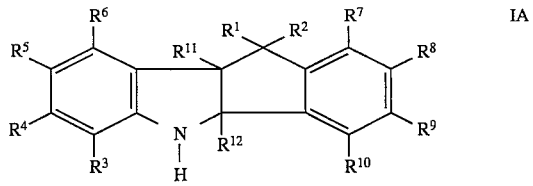

or

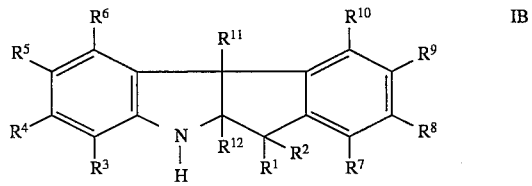

and pharmaceutically acceptable salts thereof wherein each of $R^1$, $R^2$, $R^3$, $R^4$, $R^6$, $R^7$, $R^8$, $R^9$, $R^{10}$, $R^{11}$ and $R^{12}$ is independently selected from hydrogen or an alkyl group containing 1–6 carbon atoms and $R^5$ is an alkoxy group containing 1–6 carbon atoms. The invention further concerns pharmaceutical compositions comprising the active compounds and methods employing the compounds for the treatment of conditions associated with free radical formation.

27 Claims, No Drawings

TETRAHYDROINDENOINDOLE COMPOUNDS USEFUL IN THE TREATMENT OF CONDITIONS ASSOCIATED WITH FREE RADICAL FORMATION

This application is a continuation of application Ser. No. 07/776,658, filed Oct. 15, 1991, now abandoned, which is a continuation-in-part of application Ser. No. 07/709,660, filed Jun. 3, 1991, (abandoned), which is a continuation of application Ser. No. 07/542,511, filed Jun. 22, 1990 (abandoned).

FIELD OF THE INVENTION

The present invention relates to a novel type of hydrophobic antioxidant, based on the indenoindole structure, which is highly efficient in reducing, i.e. quenching, free radicals in lipids or lipid biphases, thereby terminating the lipid peroxidation process and preventing conditions and diseases initiated by this or related processes. The invention also relates to compositions, especially pharmaceutical compositions, containing at least one compound of the invention, or a salt thereof, especially a therapeutically acceptable salt thereof, as active ingredient. In a further aspect, the invention relates to processes for the preparation of such compounds and to the use of the active compounds in medical therapy and prevention as well as in non-medical applications. Especially important in non-medical applications would be the use in controlling or terminating free-radical mediated processes.

BACKGROUND OF THE INVENTION

Some biological processes generate more or less stable intermediates that contain an unpaired electron, which can either be donated, or paired with an additional electron from the surroundings. Such intermediates are called free radicals, and they may be the products of various enzymatic and non-enzymatic reactions, some of which are vital for body functions, e.g. reduction of ribonucleoside diphosphates for DNA synthesis and the generation of prostaglandins in the prostaglandin synthase reaction. The latter is essential for inflammatory response following cell injury, and a number of other functions. Other radical reactions include the myeloperoxidase reaction in neutrophils and macrophages which destroy bacteria and other invading particles, and the electron transport in the mitochondrial respiratory chain. Most organisms contain chemical antioxidants such as α-tocopherol (vitamin E), ascorbic acid and different radical and peroxide-inactivating enzymes, e.g. superoxide dismutase, catalase and glutathione peroxidase.

Free radicals of various types are becoming increasingly associated with a broad range of conditions and diseases such as ischemic or reperfusion injury, atherosclerosis, thrombosis and embolism, allergic/inflammatory conditions such as broncial asthma, rheumatoid arthritis, conditions related to Alzheimer's disease, Parkinson's disease and ageing, cataract, diabetes, neoplasms and toxicity of antineoplastic or immunosuppresive agents and chemicals. One possible explanation for these conditions and diseases is that, for unknown reasons, the endogeneous protecting agents against radical damage are not sufficiently active to protect the tissue against radical damage. Lipid peroxidation caused by excess generation of radicals may constitute one significant damaging pathway in the above conditions and diseases. Administration of additional antioxidants, which inhibit radical reactions, e.g. lipid peroxidation, would thus provide a way of preventing or curing the above conditions and diseases. The present invention describes new antioxidants of the indenoindole type that fulfil both the requirement to accumulate in membranes, i.e. they are sufficiently hydrophobic, and they are potent inhibitors of lipid peroxidation. These new antioxidants compare favourably with other antioxidants, e.g. α-tocopherol. The compounds of the present invention may also be used in non-medical applications for stabilising compounds susceptible to oxidative deterioration, e.g. in skin care products, food preservation, food additives and for preservation of other products. The present invention extends to both a method of stabilisation using the tetrahydroindenoindoles and the resulting stabilised compositions.

Prior art

N-Methyl-4b,5,9b,10-tetrahydroindeno[1,2-b]indole is disclosed in J. Chem. Soc. Chem. Commun. p. 647–48. (1981)

4b,5,9b,10-tetrahydro-9b-ethylindeno[1,2-b]indole is disclosed in Beilsteins Handbuch Der Organischen Chemie, 4:e Auflage, It. 20 EII, p. 310–311 (1953).

DISCLOSURE OF THE INVENTION

It has been found that compounds with the tetrahydroindenoindole structures of formulae IA (THII) and IB (iso-THII) are effective as inhibitors of the lipid peroxidation process and useful as antioxidants, IA or IB may be present as a racemic mixture or in the enantiomeric form,

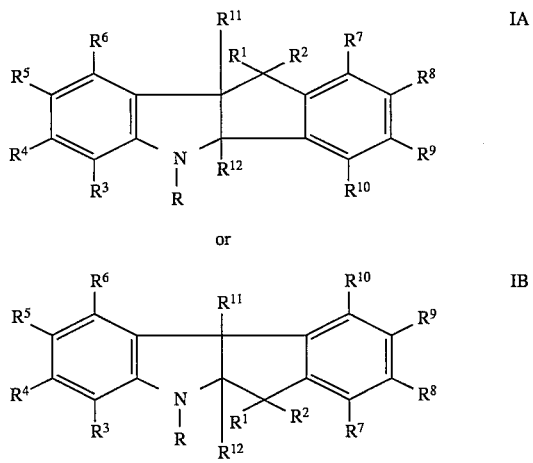

wherein

R is hydrogen, an alkyl group or $COR^{15}$, $R^1$, $R^2$, $R^{11}$ and $R^{12}$ are independently selected from hydrogen, or a lower alkyl group, $R^3$, $R^4$, $R^5$ and $R^6$ are independently selected from hydrogen hydroxy, halogen, a lower alkyl group, a lower alkoxy group, a mono- or di-lower alkylamino group, $NH_2$ or $NR^{13}COR^{14}$, $R^7$, $R^8$, $R^9$ and $R^{10}$ are independently selected from hydrogen, hydroxy, a lower alkyl group, a lower alkoxy group, a mono- or di-lower alkylamino group, $NH_2$ or $NR^{13}COR^{14}$, $R^{13}$, $R^{14}$ and $R^{15}$ independently selected from are hydrogen or a lower alkyl group, with the proviso that when R is $COR^{14}$ then at least one of $R^3$ to $R^{10}$ are hydroxy or a mono- or di-lower alkylamino group, and enantiomers or salts thereof.

The novel compounds of the present invention have either the formulae IA or IB

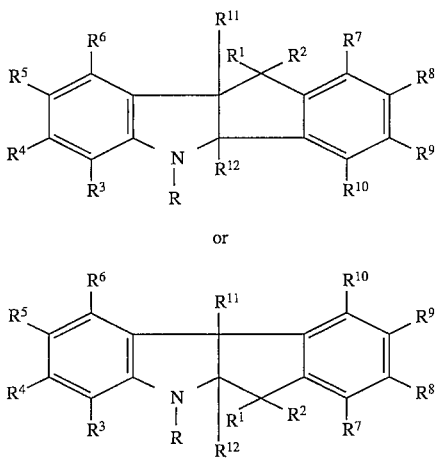

wherein

R is hydrogen an alkyl group or COR$^{15}$,

R$^1$, R$^2$, R$^{11}$ and R$^{12}$ are independently selected from hydrogen, or a lower alkyl group, R$^3$, R$^4$, R$^5$ and R$^6$ are independently selected from hydrogen hydroxy, halogen, a lower alkyl group, a lower alkoxy group, a mono- or di-lower alkylamino group, NH$_2$ or NR$^{13}$COR$^{14}$, R$^7$, R$^8$, R$^9$ and R$^{10}$ are independently selected from hydrogen, hydroxy, a lower alkyl group, a lower alkoxy group, a mono- or di-lower alkylamino group, NH$_2$ or NR$^{13}$COR$^{14}$, R$^{13}$, R$^{14}$ and R$^{15}$ are independently selected from hydrogen or a lower alkyl group, with the following provisos:

i) when R is methyl in formula IA then at least one of the radicals R$^1$ to R$^{12}$ is not hydrogen;

ii) when R is hydrogen and R$^{11}$ is ethyl in formula IA then at least one of the radicals R$^1$ to R$^{10}$ or R$^{12}$ is not hydrogen, and enantiomers and salts thereof.

The following compounds of formulae IA (THII) and IB (iso-THII) which are effective as inhibitors of the lipid peroxidation process are particularly useful as antioxidants in the medical therapy,

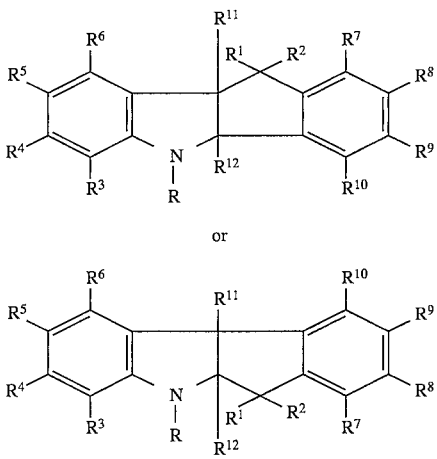

wherein

R is hydrogen, an alkyl group or COR$^{15}$,

R$^1$, R$^2$, R$^{11}$ and R$^{12}$ are independently selected from hydrogen, or a lower alkyl group, R$^3$, R$^4$, R$^5$ and R$^6$ are independently selected from hydrogen hydroxy, halogen, a lower alkyl group, a lower alkoxy group, a mono- or di-lower alkylamino group, NH$_2$ or NR$^{13}$COR$^{14}$, R$^7$, R$^8$, R$^9$ and R$^{10}$ are independently selected from hydrogen, hydroxy, a lower alkyl group, a lower alkoxy group, a mono- or di-lower alkylamino group, NH$_2$ or NR$^{13}$COR$^{14}$, R$^{13}$, R$^{14}$ and are independently selected from hydrogen or a lower alkyl group, with the proviso that when R is COR$^{15}$ then at least one of R$^3$ to R$^{10}$ are hydroxy or a mono- or di-lower alkylamino group, and enantiomers and pharmaceutically acceptable salts thereof.

The indenole and iso-indenoindole structures of the present invention have the following numbering in the rings.

INDENOINDOLE STRUCTURE

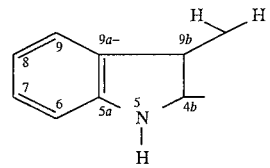

4b,5,9b,10-Tetrahydroindeno[1,2-b]indole(THII)

ISO-INDENOINDOLE STRUCTURE

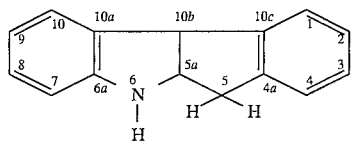

5,5A,6,10b-tetrahydroindeno[2,1-b]indole(iso-THII)

The alkyl group in the definition of R is an alkyl group having 1–24 carbon atoms e.g. methyl, ethyl, n-propyl, iso-propyl, n-butyl, sec-butyl, tert-butyl, pentyl, hexadecyl, octadecyl.

The term "lower" in the definition of substituents in the compound of the present invention means a number of carbon atoms not more than 6, preferably not more than 4.

The lower alkyl group in the definition of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$ and R$^{15}$ is an alkyl group having 1–6 carbon atoms, preferably 1–4 carbon atoms e.g. methyl, ethyl, n-propyl, isopropyl, n-butyl, sec-butyl or tert-butyl, preferred are methyl and ethyl.

The lower alkoxy group in the definition of R$^3$, R$^4$, R$^5$ and R$^6$, R$^7$, R$^8$, R$^9$ and R$^{10}$ is an alkoxy group having 1–6 carbon atoms, preferably 1–4 carbon atoms e.g. methoxy, ethoxy, n-propoxy, iso-propoxy, n-butoxy, sec-butoxy or tert-butoxy, preferred are methoxy and ethoxy.

Halogen in the definition of R$^3$, R$^4$, R$^5$ and R$^6$ is chlorine bromine, iodine or fluorine.

The mono- or di-lower alkylamino group in the definition of R$^3$, R$^4$, R$^5$, R$^6$, R$^7$, R$^8$, R$^9$ and R$^{10}$ include methylamino, dimethylamino, ethylamino, diethylamino, propylamino, dipropylamino, butylamino, dibutylamino, preferred are ethylamino and diethylamino.

Preferred groups of compounds of the invention are those wherein R, R$^1$, R$^2$, R$^4$, R$^6$ and R$^{10}$ are hydrogen and R$^5$ and/or R$^8$ are a lower alkoxy group, particularly methoxy and/or R$^3$, R$^5$, R$^7$, R$^9$, R$^{11}$ and/or R$^{12}$ are a lower alkyl group, particularly methyl, ethyl, i-propyl and those compounds wherein $R^5$ and/or $R^8$ are a mono- or di-alkylamino group, particularly ethylamino or diethylamino.

Further preferred compounds of the invention are those wherein $R^3$, $R^4$, $R^6$, $R^{11}$, $R^{12}$ is each a lower alkyl group, preferably methyl, $R^5$ is a lower alkoxy group, preferably methoxy and R, $R^1$, $R^2$, $R^7$, $R^8$, $R^9$ and $R^{10}$ is each hydrogen and those wherein R, $R^1$, $R^2$, $R^4$, $R^6$, $R^7$, $R^8$, $R^9$ and $R^{10}$ is each hydrogen, $R^5$ is a lower alkoxy group, preferably methoxy and $R^3$ is a lower alkyl group, preferably methyl.

Further preferred compounds of the invention are those wherein $R^5$ is methoxy or ethoxy and those of formula 1A wherein $R^5$ is a lower alkoxy group, preferably methoxy or ethoxy, $R^{11}$ and $R^{12}$ are either both hydrogen or both a lower alkyl group, preferably methyl, $R^3$, $R^4$ and $R^6$, which may be the same or different, are hydrogen or a lower alkyl group, preferably methyl and R, $R^1$, $R^2$, $R^7$, $R^8$, $R^9$ and $R^{10}$ is each hydrogen.

Examples of compounds of the tetrahydroindenoindoles having the formulae IA and IB, which are included in the present invention are the following:

cis-4b,5,9b,10-tetrahydroindeno[1,2-b]indole
cis-4b,5,9b,10-tetrahydro-6,8-dimethylindeno[1,2-b]indole
cis-4b,5,9b,10-tetrahydro-5,8-dimethylindeno[1,2-b]indole
cis-4b,5,9b,10-tetrahydro-8-methylindeno[1,2-b]indole
cis-4b,5,9b,10-tetrahydro-4b,6,8,9b,tetramethylindeno[1,2b]indole
cis-4b,5,9b,10-tetrahydro-8-isopropylindeno[1,2-b]indole
cis-4b,5,9b,10-tetrahydro-8-methoxy-5-methylindeno[1,2-b]indole
cis-4b,5,9b,10-tetrahydro-8-methoxyindeno[1,2-b]indole
cis-4b,5,9b,10-tetrahydro-10,10-dimethylindeno[1,2-b]indole
cis-4b,5,9b,10-tetrahydro-9b-methylindeno[1,2-b]indole
cis-4b,5,9b,10-tetrahydro-4b,9b-dimethylindeno[1,2-b]indole
cis-4b,5,9b,10-tetrahydro-4b,5,9b,trimethylindeno[1,2-b]indole
cis-4b,5,9b,10-tetrahydro-2-methoxy-1,3-dimethylindeno[1,2-b]indole
cis-4b,5,9b,10-tetrahydro-2-methoxy-1,3-dimethyl-8-isopropylindeno[1,2-b]indole
cis-4b,5,9b,10-tetrahydro-4b-methylindeno[1,2-b]indole
cis-4b,5,9b,10-tetrahydro-2-hydroxy-1,3-dimethyl-8-isopropylindeno[1,2-b]indole
cis-4b,5,9b,10-tetrahydro-2-hydroxy-1,3-dimethylindeno[1,2-b]indole
cis-4b,5,9b,10-tetrahydro-4b,8,9b-trimethylindeno[1,2-b]indole
cis-4b,5,9b,10-tetrahydro-8-isopropyl-4b,9b-dimethylindeno[1,2-b]indole
cis-4b,5,9b,10-tetrahydro-8-isopropyl-4b-methylindeno[1,2-b]indole
cis-4b,5,9b,10-tetrahydro-2,8-dimethoxy-1,3-dimethylindeno[1,2-b]indole
cis-4b,5,9b,10-tetrahydro-4b,5,8,9b-tetramethylindeno[1,2-b]indole
cis-4b,5,9b,10-tetrahydro-8-tert.butylindeno[1,2-b]indole
cis-4b,5,9b,10-tetrahydro-8-methoxy-7,9-dimethylindeno[1,2-b]indole
cis-4b,5,9b,10-tetrahydro-8-methoxy-6-methylindeno[1,2-b]indole
cis-4b,5,9b,10-tetrahydro-8-diethylamino-5-ethylindeno[1,2-b]indole
cis-4b,5,9b,10-tetrahydro-2-diethylaminoindeno[1,2-b]indole
cis-4b,5,9b,10-tetrahydro-8-tert.butyl-4b-methylindeno[1,2-b]indole
cis-4b,5,9b,10-tetrahydro-8-fluoroindeno[1,2-b]indole
cis-5,5a,6,10b-tetrahydroindeno[2,1-b]indole
cis-5,5a,6,10b-tetrahydro-9-methoxyindeno[2,1-b]indole
cis-5,5a,6,10b-tetrahydro-9-isopropylindeno[2,1-b]indole
cis-4b,5,9b,10-tetrahydro-8-methoxy-4b,6-dimethylindeno[1,2-b]indole
cis-4b,5,9b,10-tetrahydro-8-methoxy-4b,5,6-trimethylindeno[1,2-b]indole
cis-4b,5,9b,10-tetrahydro-8-methoxy-5,6-dimethylindeno[1,2-b]indole
cis-4b,5,9b,10-tetrahydro-8-methoxy-6-isopropylindeno[1,2-b]indole
cis-4b,5,9b,10-tetrahydro-8-methoxy-4b-methyl-6-isopropylindeno[1,2-b]indole
cis-4b,5,9b,10-tetrahydro-8-methoxy-4,6-dimethylindeno[1,2-b]indole
cis-4b,5,9b,10-tetrahydro-8-methoxy-4,4b,6-trimethylindeno[1,2-b]indole
cis-4b,5,9b,10-tetrahydro-4b,5,6,8,9b-pentamethylindeno[1,2-b]indole
cis-4b,5,9b,10-tetrahydro-8-diethylamino-6-methylindeno[1,2-b]indole
cis-4b,5,9b,10-tetrahydro-8-diethylamino-4b,6-dimethylindeno[1,2-b]indole
cis-4b,5,9b,10-tetrahydro-8-diethylamino-4b,5,6-trimethylindeno[1,2-b]indole
cis-4b,5,9b,10-tetrahydro-8-methoxy-6,10,10-trimethylindeno[1,2-b]indole
cis-4b,5,9b,10-tetrahydro-8-methoxy,4b,6,10,10-tetramethylindeno[1,2-b]indole
cis-4b,5,9b,10-tetrahydro-8-diethylamino-6,10,10-trimethylindeno[1,2-b]indole
cis-4b,5,9b,10-tetrahydro-8-diethylamino-4b,6,10,10-tetramethylindeno[1,2-b]indole
cis-4b,5,9b,10-tetrahydro-8-hydroxy-7,9-dimethylindeno[1,2-b]indole
cis-4b,5,9b,10-tetrahydro-8-hydroxy-4b,7,9-trimethylindeno[1,2-b]indole
cis-4b,5,9b,10-tetrahydro-8-hydroxy-7,9-ditert.butylindeno[1.2-b]indole
cis-4b,5,9b,10-tetrahydro-8-hydroxy-6,7,9-trimethylindeno[1,2-b]indole
cis-4b,5,9b,10-tetrahydro-8-hydroxy-4b,6,7,9-tetramethylindeno[1,2-b]indole
cis-4b,5,9b,10-tetrahydro-8-methoxy-4b,6,9b-trimethylindeno[1,2-b]indole
cis-4b,5,9b,10-tetrahydro-8-methoxy-4b,5,6,9b-tetramethylindeno[1,2-b]indole
cis-4b,5,9b,10-tetrahydro-8-diethylamino-4b,6,9b-trimethylindeno[1,2-b]indole
cis-4b,5,9b,10-tetrahydro-8-diethylamino-4b,5,6,9b-tetramethylindeno[1,2-b]indole
cis-5,5a,6,10b-tetrahydro-9-methoxy-7-methylindeno[2,1-b]indole,
cis-5,5a,6,10b-tetrahydro-9-methoxy-5a,7-dimethylindeno[2,1-b]indole
cis-5,5a,6,10b-tetrahydro-9-diethylamino-7-methylindeno[2,1-b]indole
cis-5,5a,6,10b-tetrahydro-9-diethylamino-5a,7-dimethylindeno[2,1-b]indole
cis-5,5a,6,10b-tetrahydro-9-hydroxy-8,10-dimethylindeno[2,1-b]indole
cis-5,5a,6,10b-tetrahydro-9-hydroxy-7,8,10-trimethylindeno[2,1-b]indole
cis-5,5a,6,10b-tetrahydro-9-hydroxy-5a,7,8,10-tetramethylindeno[2,1-b]indole
cis-5,5a,6,10b-tetrahydro-9-diethylaminoindeno[2,1-b]indole cis-4b,5,9b,10-tetrahydro-6-isopropylindeno[1,2-b]indole
cis-5,5a,6,10b-tetrahydro-9-methoxy-5,5,7-trimethylindeno[2,1-b]indole
cis-5,5a,6,10b-tetrahydro-9-diethylamino-5,5,7-trimethylindeno[2,1-b]indole
cis-4b,5,9b,10-tetrahydro-2-diethylamino-8-methoxy-6-methylindeno[1,2-b]indole
cis-4b,5,9b,10-tetrahydro-8-methoxy-4b-isopropylindeno[1,2-b]indole
cis-4b,5,9b,10-tetrahydro-8-methoxy-4b-isopropyl-6-methylindeno[1,2-b]indole
cis-4b,5,9b,10-tetrahydro-8-isopropyl-5-methylindeno[1,2-b]indole
cis-4b,5,9b,10-tetrahydro-8-methoxy-6-ethylindeno[1,2-b]indole
cis-4b,5,9b,10-tetrahydro-3-methoxy-4b-methylindeno[1,2-b]indole
cis-4b,5,9b,10-tetrahydro-7-methoxy-4b-methylindeno[1,2-b]indole
cis-5,5b,6,10b,tetrahydro-3-hydroxy-2,4-dimethylindeno[2,1-b]
cis-4b,5,9b,10-tetrahydro-8-acetamido-6-methylindeno[1,2-b]indole
cis-4b,5,9b,10-tetrahydro-2-acetamido-8-methoxy-6-methylindeno[1,2-b]indole
cis-4b,5,9b,10-tetrahydro-8-tert.butyl-5-methylindeno[1,2-b]indole
cis-5,5b,6,10b tetrahydro-3-acetamidoindeno[2,1-b]indole
cis-4b,5,9b,10-tetrahydro-2-acetamidoindeno[1,2-b]indole
cis-5,5a,6,10b-tetrahydro-6-methylindeno[2,1-b]indole
cis-5,5a,6,10b-tetrahydro-6-ethyl-9-isopropylindeno[2,1-b]indole
cis-5,5a,6,10b-tetrahydro-9-fluoroindeno[2,1-b]indole
cis-5,5a,6,10b-tetrahydro-9-tert.butylindeno[2,1-b]indole Preferred tetrahydroindenoindole compounds of the present invention having antioxidant activity are the following:
cis-4b,5,9b,10-tetrahydroindeno[1,2-b]indole
cis-4b,5,9b,10-tetrahydro-6,8-dimethylindeno[1,2-b]indole
cis-4b,5,9b,10-tetrahydro-5,8-dimethylindeno[1,2-b]indole
cis-4b,5,9b,10-tetrahydro-8-methylindeno[1,2-b]indole
cis-4b,5,9b,10-tetrahydro-4b,6,8,9b,tetramethylindeno[1,2-b]indole
cis-4b,5,9b,10-tetrahydro-8-isopropylindeno[1,2-b]indole
cis-4b,5,9b,10-tetrahydro-8-methoxy-5-methylindeno[1,2-b]indole
cis-4b,5,9b,10-tetrahydro-8-methoxyindeno[1,2-b]indole
cis-4b,5,9b,10-tetrahydro-10,10-dimethylindeno[1,2-b]indole
cis-4b,5,9b,10-tetrahydro-9b-methylindeno[1,2-b]indole
cis-4b,5,9b,10-tetrahydro-4b,9b-dimethylindeno[1,2-b]indole
cis-4b,5,9b,10-tetrahydro-4b,5,9b,trimethylindeno[1,2-b]indole
cis-4b,5,9b,10-tetrahydro-2-methoxy-1,3-dimethylindeno[1,2-b]indole
cis-4b,5,9b,10-tetrahydro-2-methoxy-1,3-dimethyl-8-isopropylindeno[1,2-b]indole
cis-4b,5,9b,10-tetrahydro-4b-methylindeno[1,2-b]indole
cis-4b,5,9b,10-tetrahydro-2-hydroxy-1,3-dimethyl-8-isopropylindeno[1,2-b]indole
cis-4b,5,9b,10-tetrahydro-2-hydroxy-1,3-dimethylindeno[1,2-b]indole
cis-4b,5,9b,10-tetrahydro-4b,8,9b-trimethylindeno[1,2-b]indole
cis-4b,5,9b,10-tetrahydro-8-isopropyl-4b,9b-dimethylindeno[1,2-b]indole
cis-4b,5,9b,10-tetrahydro-8-isopropyl-4b-methylindeno[1,2-b]indole
cis-4b,5,9b,10-tetrahydro-2,8-dimethoxy-1,3-dimethylindeno[1,2-b]indole
cis-4b,5,9b,10-tetrahydro-4b,5,8,9b-tetramethylindeno[1,2-b]indole
cis-4b,5,9b,10-tetrahydro-8-tert.butylindeno[1,2-b]indole
cis-4b,5,9b,10-tetrahydro-8-methoxy-7,9-dimethylindeno[1,2-b]indole
cis-4b,5,9b,10-tetrahydro-8-methoxy-6-methylindeno[1,2-b]indole
cis-4b,5,9b,10-tetrahydro-8-diethylamino-5-ethylindeno[1,2-b]indole
cis-4b,5,9b,10-tetrahydro-2-diethylaminoindeno[1,2-b]indole
cis-4b,5,9b,10-tetrahydro-8-tert.butyl-4b-methylindeno[1,2-b]indole
cis-4b,5,9b,10-tetrahydro-8-fluoroindeno[1,2-b]indole
cis-5,5a,6,10b-tetrahydroindeno[2,1-b]indole
cis-5,5a,6,10b-tetrahydro-9-methoxyindeno[2,1-b]indole
cis-5,5a,6,10b-tetrahydro-9-isopropylindeno[2,1-b]indole Particularly preferred compounds are cis-4b,5,9b,10-tetrahydro-4b,6,7,9,9b-pentamethyl-8-methoxyindeno(1,2-b)indole;
cis-5,5a,6,10-tetrahydro-7-methyl-9-methoxyindeno(2,1-b)indole;
cis-4b,5,9b,10-tetrahydro-4b,6,8,9b-tetramethylindeno[1,2-b]indole;
cis-4b,5,9b,10-tetrahydro-8-methoxy-4b,6,9b-trimethylindeno[1,2-b]indole;
cis-4b,5,9b,10-tetrahydro-8-ethoxy-4b,7,9,9b-tetramethylindeno[1,2-b]indole; or
cis-4b,5,9b,10-tetrahydro-8-methoxy-6,7,9-trimethylindeno[1,2-b]indole.

The compounds having formula IA and IB can exist either as such or as pharmaceutically acceptable salts.

For the compounds with the general formula IA and IB which are asymmetric, both the pure enantiomers, mixtures of enantiomers and the racemic mixtures are within the scope of the present invention.

Pharmaceutical preparations

According to the present invention the compounds of the formula IA or IB will normally be administered orally, rectally, dermally or by injection, in the form of pharmaceutical preparations comprising the active ingredient either as a free base or a pharmaceutically acceptable nontoxic acid addition salt, e.g. the hydrochloride, hydrobromide, lactate, acetate, phosphate, sulfate, sulfamate, citrate, tartrate, oxalate and the like in a pharmaceutically acceptable dosage form.

The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration. Dermal administration would normally utilize 0.1–5% by weight of the active ingredient in a suitable vehicle.

To produce pharmaceutical preparations containing a compound of the formula I in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the abovementioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutic treatment of humans are about 0.01–100 mg/kg body weight at peroral administration and 0.001–100 mg/kg body weight at parenteral administration.

Method of Preparation

The compounds of the invention may be prepared as outlined below, however, the invention is not limited to these methods, the compounds may be prepared by processes described in known art.

Methods involving preparation of THII and iso-THII compounds from non THII or iso-THII materials.

a. 4b,5,9b,10-tetrahydroindeno[1,2-b]indole (THII, IA) and analogues containing functional groups on the atoms of the benzenoid rings and/or radicals at C-10 such as lower alkyl, lower alkoxy, may be prepared by reduction of corresponding 5,10-dihydroindeno[1,2-b]indole (DHII)

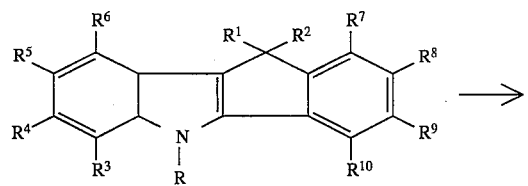

XI

-continued

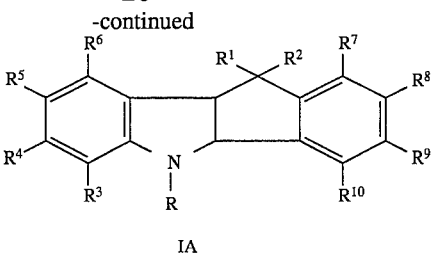

IA $R, R^1, R^2, R^3, R^4, R^5, R^6, R^7, R^8, R^9$ and $R^{10}$, are as defined under formula IA.

DHII or an analogues are reduced by reaction with zinc and an aqueous mineral acid, such as hydrochloric acid, or more efficiently by reaction with a boron based reductant such as sodium cyanoborohydride in a solvent, often acetic acid or $BH_3$ in tetrahydrofurane. Alternatively morpholino borane in a solvent, often tetrahydrofurane or dioxane, and in the presence of a strong acid e.g. hydrochloric acid, can be used. Alternatively a trialkylsilane can be used. At the end of the reaction the product is isolated by dilution of the reaction mixture with water, neutralisation, and either filtration or solvent extraction. Alternatively reduction is achieved by hydrogenation over a catalyst such as palladium, in this case the DHII compound is dissolved in a suitable solvent, for example ethanol, acetic acid, or ethyl acetate. In such case the product is isolated by removal of the catalyst and evaporation of the solvent under reduced pressure. THII and its analogues may be purified by crystallisation from a suitable solvent, or by column chromatography using silica. DHII and its analogues are synthesized by the Fischer indolisation reaction from phenylhydrazines of formula II and 1-indanones of formula III, wherein $R^{11}$ is hydrogen. 5-Alkyl-4b,5,9b,10-tetrahydroindeno[1,2-b]indoles (N-Alkyl THIIs) are either obtained by the N-alkylation of the corresponding DHII compounds prior to reduction, or from the corresponding 5H-THII compounds by direct N-alkylation. In both cases it is preferable to form the intermediate anions of the tetracyclic amines by treating them with base prior to reaction with an alkyl halide or an alkyl sulphate.

b. 4b,5,9b,10-tetrahydroindeno[1,2-b]indole and analogues bearing a substituent at C-9b can be synthesized by the Fischer indolisation followed by reduction of the intermediate indolenines (IV)

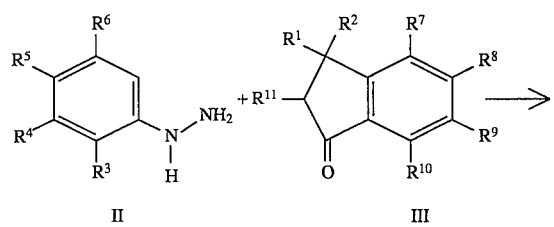

II          III

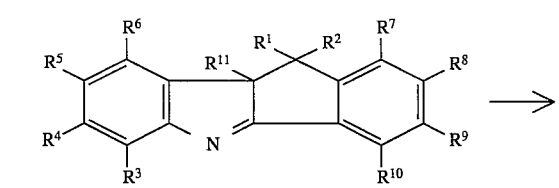

IV

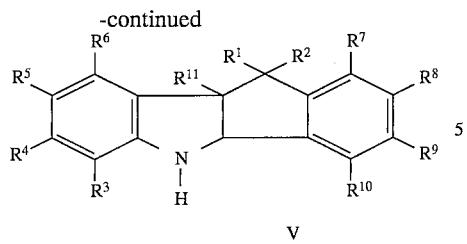

V $R^1$, $R^2$, $R^3$, $R^4$, $R^5$, $R^6$, $R^7$, $R^8$, $R^9$, $R^{10}$, and $R^{11}$, are as defined under formula IA, and if appropriate followed by N-alkylation with R-halide or R-sulphate, where R is as defined in formula IA.

2-Substituted-1-indanones (III) or equivalent starting materials, with appropriate functional group substitution in the benzenoid ring and at C-3, may be reacted with phenylhydrazines (II) either as the free base, or as a salt, often the hydrochloride. Normally the reactants are dissolved in a solvent preferably an alcoholic solvent such as ethanol or propanol. In some cases heat is not required, whereas in others it is necessary to heat the reaction mixture to reflux for up to 1 hour, or more. The phenylhydrazone product can be isolated by dilution of the reaction mixture with water and separated by filtration, or by extraction with a suitable solvent. Further purification is achieved by crystallisation or by chromatography. In the last case column chromatography on silica is satisfactory and a range of eluting solvents may be used.

Cyclisation of the phenylhydrazones to the indolenines (IV) is achieved by redissolving them in a suitable solvent, preferably an alcohol such as ethanol or propanol, and treating the solution with an acid, for example, hydrochloric acid, acetic acid, or trifluoroacetic acid. Heat may or may not be required. Other cyclisation reagents including Lewis acids such as zinc chloride, or reagents containing a phosphorus atom, for example phosphorus trichloride, phosphorus oxytrichloride, polyphosphoric acid, or polyphosphonates, can also be used.

Should the salts of phenylhydrazines be used in place of phenylhydrazines in reactions with the indanones then cyclisation of the intermediate phenylhydrazones to the indolenines may occur spontaneously.

In some instances it is observed that the phenylhydrazones obtained from the reactions of phenylhydrazines and 2-substituted-1-indanones on heating in a high boiling solvent such as diethylene glycol, afford the corresponding THII derivatives.

Reduction of the indolenines (IV) to the THII derivatives (V) substituted at C-9b is achieved using standard reducing agents such as sodium borohydride in an appropriate solvent such as ethanol. The products are then isolated and purified in the usual way.

c. 4b,9b-Dialkyl-4b,5,9b,10-tetrahydroindeno[1,2-b]indoles (VI) and analogues may be prepared directly by reacting indolenines (IV) with lithium alkyls ($R^{12}$Li) in an aprotic solvent such as dry tetrahydrofuran.

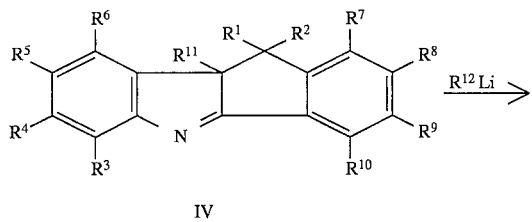

IV

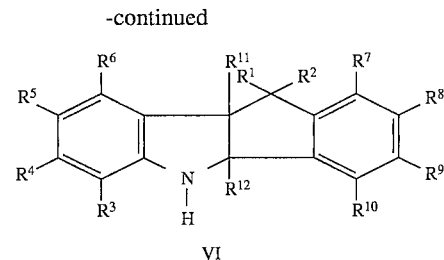

VI wherein $R^1$ to $R^{12}$ are as defined under formula IA, and if appropriate followed by N-alkylation with R-halide or R-sulphate, where R as is defined in formula IA.

d. 5,5a,6,10b-tetrahydroindeno[2,1-b]indole (iso-THII) and analogues may be prepared by reduction of the corresponding 5,6,-dihydroindeno[2,1-b]indole (iso-DHII) by the same methods as outlined in method a. above.

e. 10b-Substituted-5,5a,6,10b-tetrahydroindeno[2,1-b]indoles (IX) and analogues can be synthesised from indan-2-ones (XII) bearing a substituent group at C-3, by reacting them with suitable phenylhydrazines (II) under the same conditions as described for the preparation of the indolenines (IV). The intermediate products are the corresponding indolenines (VIII) which when dissolved in a suitable solvent, often ethanol, and reacted with a reducing agent, such as sodium borohydride, yield iso-THII compounds (IX) bearing an alkyl substituent at position 10b. These compounds can be isolated from the reaction mixtures by dilution and filtration, or by extraction with a suitable solvent.

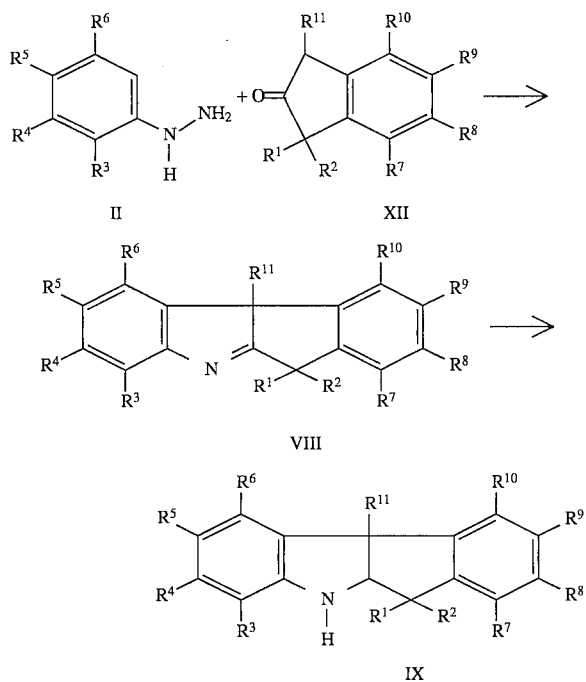

$R^1$, $R^2$, $R^3$, $R^4$, $R^5$, $R^6$, $R^7$, $R^8$, $R^9$, $R^{10}$, $R^{11}$ are as defined under formulae IB.

f. Iso-THII compounds (X) bearing alkyl substituents at C-5a and at C-10b are obtained from the corresponding indolenines (VIII), through reaction with alkyl lithiums ($R^{12}$Li). Using the same procedures, previously described for the 4b,9b dialkylated THII compounds (VI),

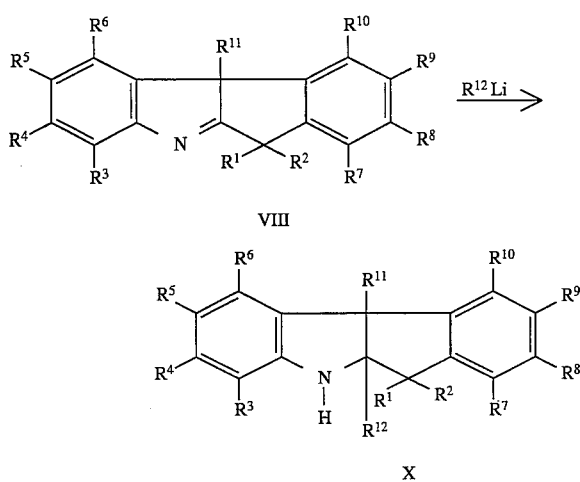

$R^1$ to $R^{12}$ is defined as under formula IB.

Methods involving preparation of THII or iso-THII compounds by modification of other THII or iso-THII compounds.

g. 5-Alkyl THII or 6-alkyl iso-THII derivatives are synthesized by N-alkylation of corresponding 5H-THII or 6H iso-THII compounds dissolved in an aprotic solvent e.g. acetone, acetonitrile, dimethylsulfoxide (DMSO), dimethylformamide (DMF) optionally but preferably in the presence of a strong base, e.g. with sodium hydride and the reaction mixture then treated with an alkyl halide or an alkyl sulphate. Alternatively the corresponding 5-alkyl DHII or 6-alkyl iso-DHII compound may be reduced by reaction with zinc and an aqueous mineral acid such as hydrochloric acid, or more efficiently by reduction with a boron based reductant such as sodium cyanoborohydride in a solvent, often acetic acid or $BH_3$ in tetrahydrofuran. Alternatively morpholino borane in a solvent, often tetrahydrofuran or dioxane, and in the presence of a strong acid e.g. hydrochloric acid, can be used. Alternatively a trialkyl silane can be used. At the end of the reaction the product is isolated by dilution with water and either filtration or solvent extraction. Alternatively reduction may be achieved by hydrogenation over a catalyst such as palladium, in this case the 5-alkyl-DHII or the 6-alkyl iso-DHII compound is dissolved in a suitable solvent, for example, ethanol, acetic acid, or ethyl acetate. In such a case the product is isolated by removal of the catalyst and evaporation of the solvent under reduced pressure. 5-Alkyl-THII or 6-alkyl iso-THII compounds may be purified by crystallisation from a suitable solvent, or by column chromatography using silica.

h. 5-Alkyl THII or 6-alkyl iso-THII are synthesized by simple reduction of the corresponding 5-aryl or 6-aryl derivatives using standard methods e.g. by use of lithium-aluminium hydride.

i. THII or iso-THII compounds with alkylamino groups in $R^3$–$R^6$ and/or $R^7$–$R^{10}$ can be prepared from the corresponding 5-acyl THII or 6-acyl iso-THII nitro compounds by standard reduction techniques, e.g. using $TiCl_3$/HCl, followed by one standard N-alkylation, optionally followed by acidic hydrolysis of the 5- or 6-acyl groups for generation of 5- or 6-unsubstituted compounds The nitro compounds used can either be prepared from the corresponding DHII or iso-DHII-compounds according to methods a. or d. above or via nitration of suitably substituted THII or iso-THII compounds.

j. Hydroxy substituted compounds can be prepared from the corresponding alkoxy substituted ones by standard ether dealkylation methods, e.g. using different Lewis acids.

k. 4b-Alkyl THII and iso-THII i.e. wherein $R^{12}$ is a lower alkyl group and R, $R^1$ to $R^{11}$ are as defined in formula I can be prepared from the corresponding 4b-unsubstituted analogue by a sequence of metallation, e.g. using butyl lithium, carbonation with carbon dioxide, a second directed metallation, e.g. using butyl lithium, and an alkylation with $R^{12}$-halide or $R^{12}$-sulphate followed by a final hydrolysis of the resulting N-carboxylated intermediate.

Processes for preparation of starting materials such as 5,10-dihydroindeno[1,2-b]indole (DHII) and 5,6-dihydroindeno[2,1-b]indole and analogues containing functional groups are described in our application EP-A-0 404 536.

The following illustrates the principle and the adaption of the invention, however, without being limited thereto. Temperature is given degrees Celsius.

WORKING EXAMPLES

EXAMPLE 1 cis-4b,5,9b,10-Tetrahydroindeno[1,2-b]indole

To a suspension of 5,10-dihydroindeno[1,2-b]indole 9.16 g, 93 mmol in glacial acetic acid (300 cm$^3$) was added portionwise over half an hour, sodium cyanoborohydride (24 g, 400 mmol). The mixture was stirred for 3 hours, until all the material had dissolved. The solution was poured into ice water (500 cm$^3$) and stirred for 1 hour to break down the borohydride complex. The clear solution was carefully neutralised with sodium hydroxide causing a white precipitate to form. This was filtered and washed with water until the washings were free from cyanide ion. Drying yielded the title compound as a white solid. Yield: 19 g, (98%). M.p. 107° C. $^1$H NMR (CDCl$_3$) δ: 3.20 (1H, dd,), 3.51 (1H, dd), 3.99 1H, br,) 4.18 (1H, ddd,), 5.25 (1H, d), 6.60 (1H, d,), 6.74 (1H, dd,), 6.99 (1H, dd,), 7.15–7.22 (4H, m,), 7.32 (1H, d,),

EXAMPLE 2 cis-4b,5,9b,10-Tetrahydro-5-methylindeno[1,2-b]indole

A flame dried flask was charged with sodium hydride (60 mg, 2.5 mmol), and tetrahydrofuran (THF) (5 cm$^3$) protected under an atmosphere of nitrogen. To the stirring suspension was added cis-4b,5,9b,10-tetrahydroindeno[1,2-b]indole (500 mg, 2.4 mmol) in THF (5 cm$^3$) dropwise. The reaction was stirred for 1 hour, a pink colour developing. Iodomethane (0.2 cm$^3$) was added, and the solution was stirred overnight. Water (5 cm$^3$) was added, and the THF removed in vacuo. The colourless solid thus obtained was filtered, and dried in a vacuum desiccator. The product was dissolved in 5% ethyl acetate petrol (60°–80° C.) and filtered through a pad of flash silica. After evaporation of the solvent in vacuo, the title compound was obtained as a colourless solid. Yield: 450 mg (85%). M.p. 76°–77° C. $^1$H NMR (CDCl$_3$) δ: 3.0 (3H, s,), 3.1 (1H, dd,), 3.4 (1H, dd,), 4.1 (1H, ddd,), 4.9 (1H, d,), 6.4 (1H, d,), 6.7 (1H, dd,), 7.1–7.5 (6H, m,).

EXAMPLE 3 cis-4b,5,9b,10-Tetrahydro-8-methoxyindeno[1,2-b]indole 5,10-Dihydro-8-methoxyindeno[1,2-b]indole (770 mg, 3.3 mmol) was reacted with sodium cyanoborohydride (1.0 g, 16 mmol), in glacial acetic acid (17 cm$^3$) solution. After 30 minutes, the solution was poured into ice/water, stirred for 1 hour, and neutralised with sodium hydroxide. The colourless reaction mixture was extracted into diethylether, the organic layers, dried (Na$_2$SO$_4$), and concentrated in vacuo. The residue was column chromatographed (10% ethyl acetate/petrol 60°–80° C.) to yield the title compound as a colourless solid. Yield: 520 mg (66%). M.p. 101° C. $^1$H NMR (CDCl$_3$) δ: 3.28 (1H, dd,), 3.57 (1H, dd,), 3.80 (3H, s,), 3.85 (1H, br,), 4.24 (1H, dd,), 5.30 (1H, d,), 6.6–7.4 (7H, m,).

EXAMPLE 4 cis-4b.5.9b,10-Tetrahydro-8-methoxy-5-methylindeno[1,2-b]indole

Using the same procedure as described in Example 2 for cis-4b,5,9b,10-tetrahydro-8-methoxyindeno[1,2-b]indole (239 mg, 1.0 mmol) was methylated with iodomethane, using sodium hydride (25 mg, 1.1 mmol) as the base, in THF (2 cm$^3$). Extraction work-up (into diethylether), and purification by "suction" flash chromatography, yielded a clear gum. Yield: 158 mg, (63%) which solidified after bulb to bulb distillation (180° C. at 0.2 mm Hg), giving the title compound M.p. 72° C. $^1$H NMR (CDCl$_3$) δ: 2.87 (3H, s,), 3.03 (1H, dd,), 3.36 (1H, dd,), 3.70 (3H, s,), 4.08 (1H, ddd,), 4.80 (1H, d,), 6.28 (1H, d,), 6.61 (1H, dd,), 6.77 (1H, dd,), 7.1–7.5 (4H, m,).

EXAMPLE 5 cis-5,5a,6,10b-Tetrahydroindeno[2,1-b]indole 5,6-Dihydroindeno[2,1-b]indole (185 mg, 0.9 mmol) was reacted with sodium cyanoborohydride (310 mg, 5 mmol), in glacial acetic acid (5 cm$^3$), for six hours. The solution was poured into ice/water, and stirred for one hour. It was then neutralised with sodium hydroxide, and the white solid which formed was collected by filtration, washed with water, dried and purified by "flash" chromatography (10% EtOAc/petrol 60°–80° C., R$_f$ 30% EtOAc/petrol (60°–80° C.) 0.6) to yield the title compound as a colourless solid. Yield: (81 mg, 43%) M.p. 85°–86° C. $^1$H NMR (CDCl$_3$) δ: 3.09 (1H, dd,), 3.33 (1H, dd,), 3.45 (1H, br,), 4.74 (1H, d,), 4.82 (1H, ddd,), 6.55 (1H, d,), 6.73 (1H, ddd,), 7.00 (1H, ddd,), 7.1–7.4 (4H, m).

EXAMPLE 6 cis-4b,5,9b,10-Tetrahydro-10,10-dimethylindeno[1,2-b]indole 5,10-Dihydro-10,10-dimethylindeno [1,2-b]indole (1.00 g, 4.29 mmol) was reacted with sodium cyanoborohydride (1.0 g, 16 mmol) in glacial acetic acid (20 cm$^3$), for 10 minutes. The solution was poured into water, stirred for 30 minutes, and extracted into diethylether. The organic phase was washed 10 times with water, dried (Na$_2$SO$_4$), and the solvent removed in vacuo. The residue was dissolved in 5% ethylacetate/petrol (60°–80° C.) and filtered through a pad of "flash" silica, yielding, on removal of solvent, a gum which solidified on the oil pump, to give the title compound as a colourless solid. Yield: 0.98 g, (98%) M.p. 57°–59° C. $^1$H NMR (CDCl$_3$) δ: 1.17 (3H, s,), 1.43 (3H, s,), 3.86 (1H, d,), 3.9 (1H, br,), 5.29 (1H, d,), 6.59 (1H, d,), 6.71 (1H, ddd,), 7.02 (1H, ddd,), 7.2–7.3 (5H, m,).

EXAMPLE 7 cis-4b,5,9b,10-Tetrahydro-9b-methylindeno [1,2-b]-indole

The phenylhydrazone of 2-methyl-1-indanone (1.44 g, 6.1 mmol) was heated in diethylene glycol (20 cm$^3$) to near its reflux temperature, until ammonia started to evolve from the air condenser. Heating was continued overnight, or until the ammonia ceased to evolve. The solution was cooled, poured into an equal volume of water, and extracted into diethylether. The ethereal solution was back-extracted with 2M hydrochloric acid, which was made basic with sodium hydroxide, and re-extracted with diethylether. The extracts were evaporated and the residue was purified by column chromatography using silica eluating with 5% EtOAc petrol to yield the title compound as a colourless solid (R$_f$ 30% EtOAc/petrol 0.8). Yield: (28%). M.p. 72° C. $^1$H NMR (CDCl$_3$) δ: 1.46 (3H, s,), 3.10 (1H, d), 3.30 (1H, dd,), 4.05 (1H, s,), 4.69 (1H, s,), 6.52 (1H, dd,), 6.71 (1H, ddd,), 6.95 (1H, ddd,), 7.0–7.2 (5H, m,).

EXAMPLE 8 cis-4b,5,9b,10-Tetrahydro-4b,9b-dimethylindeno[1,2-b]indole

Methyllithium (1.5 ml, 2 eq of 1.5 m solution in hexanes) was added dropwise at −78° C. to a solution of 9b,10-dihydro 9b-methylindeno[1,2-b]indole (260 mg, 1.19 mmol) in THF (10 cm$^3$). After stirring at −78° C. for one hour, water (1 cm$^3$) was added to the dark red solution, and the reaction allowed to warm. On approaching room temperature, the colour of the solution was quenched. The reaction was quenched with saturated ammonium chloride solution (10 cm$^3$), the organic phase separated, and dried (Na$_2$SO$_4$). Evaporation of solvent and "flash" chromatography (10% EtOAc/petrol [60°–80° C.]) gave a colourless gum (R$_f$10% EtOAc/petrol (60°–80° C.)] 0.5) which solidified after all remaining solvent had been removed with an oil pump to give the title compound as a colourless solid. Yield: 87 mg (31%). $^1$H NMR (CDCl$_3$) δ: 1.35 (3H, s,), 1.46 (3H, s,), 3.07 (1H, d,), 3.36 (1H, d,), 4.27 (1H, br,), 6.53 (1H,), 6.71 (1H, ddd,), 6.96 (1H, ddd,), 7.1–7.3 (5H, m,).

EXAMPLE 9 cis,4b,5,9b,10-Tetrahydro-6,8-dimethylindeno[1,2-b]indole 5,10-Dihydro-6,8-dimethylindeno[1,2-b]indole (323 mg, 1.38 mmol) was reacted with sodium cyanoborohydride (400 mg, 5 eq) in glacial acetic acid solution (7 cm$^3$) for 30 minutes. The solution was poured into ice/water, and stirred for a further 30 minutes. The aqueous solution was neutralised with sodium hydroxide, and the suspension was extracted into diethylether. The organic extracts were washed with water, dried (Na$_2$SO$_4$) and evaporated in vacuo. Purification by "suction flash" chromatography, gave the title compound as a colourless solid. Yield: 2.44 mg, (75%). M.p. 147° C. (from EtOAc/petrol [60°–80° C.]). $^1$H NMR (CDCl$_3$) δ: 2.03 and 2.07 (3H, s,), 3.18, (1H, dd,), 3.48 (1H, dd,), 4.16 (1H, ddd,), 5.24 (1H, d,), 6.66 (1H, s,), 6.84 (1H, s,), 7.1–7.4 (4H, m,).

EXAMPLE 10 cis-4b,5,9b,10-Tetrahydro-8 methylindeno[1,2-b]indole 5,10-Dihydro-8-methylindeno[1,2-b]indole (10 g, 46 mmol) was stirred at room temperature in glacial acetic acid (150 cm$^3$). Sodium cyanoborohydride (8.6 g, 3 equivalents) was added portionwise over a period of 30 minutes. The reaction was stirred for a further hour, and then poured into ice/water (200 cm$^3$). After stirring for 30 minutes, the acidic solution was made basic by the addition of sodium hydroxide, and the colourless solid thus formed collected by filtration. This solid was washed copiously with water until the residue was free from cyanide ion, and then dried in a vacuum oven to yield the title compound as a colourless solid. Yield: 7.5 g (73%) M.p. 110° C. (from ethanol/water). $^1$H NMR (CDCl$_3$) δ: 2.24 (3H, s,), 3.20 (1H, dd,), 3.50 (1H, dd,) 3.9 (1H, br,), 4.16 (1H, dd,), 5.23 (1H, d,), 6.52 (1H,d,), 6.80 (1H, d,), 6.99 (1H, s,), 7.1–7.4 (4H, m,).

EXAMPLE 11 cis-4b,5,9b,10-Tetrahydro-5,8-dimethylindeno[1,2-b]indole

A solution of 4b,5,9b,10-Tetrahydro-8-methylindeno[1,2b]indole (1.8 g, 8.1 mmol) in THF (20 cm$^3$) was cooled to −78° C., and n-butyllithium (5.6 cm$^3$ of 1.6M solution in hexane, 9.0 mmol) added dropwise. The temperature of the solution was allowed to warm to room temperature, and stirred for 30 minutes. The reaction was then cooled to −78° C., and iodomethane (0.6 cm$^3$, 0.9 mmol) added. The reaction was again allowed to warm slowly to room temperature, and then quenched with a saturated solution of ammonium chloride (5 cm$^3$). After stirring the mixture overnight, the organic layer was diluted with dichloromethane, separated, washed with brine, and dried (MgSO$_4$). After removal of solvent in vacuo, the residue was purified by column chromatography to give a gum, which gave the title compound as a colourless solid on trituration with ethanol. Yield: 1.0 g, (53%). M.p. 54° C. (from ethanol). $^1$H NMR (CDCl$_3$) δ: 2.25 (3H, s,), 2.94 (3H, s,), 3.07 (1H, dd,), 3.41 (1H, dd,), 4.11 (1H, m,), 4.88 (1H, d,), 6.30 (1H, d,), 6.88 (1H, d,), 6.96 (1H, d,), 7.1–7.4 (4H, m,).

EXAMPLE 12 cis-4b,5,9b,10-Tetrahydro-8-iso-propylindeno[1,2-b]indole 5,10-Dihydro-8-iso-propylindeno [1,2-b]indole (5.27 g, 21.3 mmol) was stirred at room temperature in glacial acetic acid (100 cm$^3$). Sodium cyanoborohydride (5 g, 3 equivalents) was added portionwise over a period of 30 minutes. The reaction was stirred for a further 30 minutes, and then poured into ice/water (150 cm$^3$). After stirring for 30 minutes, the solution was neutralised with aqueous sodium hydroxide, and the colourless solid thus formed collected by filtration. This solid was washed copiously with water until the residue was free from cyanide ion and then dried in a vacuum oven to give the title compound as a colourless solid. Yield: 3.25 g (61%). M.p. 104° C. [from petrol (60°–80° C.)]. $^1$H NMR (CDCl$_3$) δ: 1.19 (6H, d,), 2.80 (1H, septet,), 3.20 (1H, dd,), 3.48 (1H, dd,), 4.07 (1H, br,), 4.15 (1H, ddd,), 5.21 (1H, d,), 6.53 (1H, d,), 6.86 (1H, dd,), 7.03 (1H, s,), 7.1–7.4 (4H, m,).

EXAMPLE 13 cis-4b,5,9b,10-Tetrahydro-5-methyl-8-iso-propylindeno[1,2-b]indole

A solution of cis-4b,5,9b,10-tetrahydro-8-isopropylindeno[1,2-b]indole (1.75 g, 7.0 mmol) in THF (10 cm$^3$), was added to a suspension of sodium hydride (200 mg, 1.2 equivalents) in THF (7 cm$^3$), at 0° C. The reaction was stirred for two hours and iodomethane (0.53 cm$^3$, 1.2 equivalents) was added. The reaction was stirred overnight, and then quenched with a saturated solution of ammonium chloride. The organic phase was separated, and the aqueous phase extracted with diethyl ether. The combined organic phases were dried (Na$_2$SO$_4$), and solvent removed in vacuo to yield the title compound as a colourless gum which was purified by bulb to bulb distillation. Yield: 1.0 g (54%). B.p. 200° C. at 0.4 mmHg. $^1$H NMR (CDCl$_3$) δ: 1.22 (6H, d,), 2.81 (1H, septet,), 2.94 (3H, s,), 3.09 (1H, dd,), 3.43 (1H, dd,), 4.15 (1H, ddd,), 4.90 (1H, d,), 6.32 (1H, d,), 6.93 (1H, dd,), 7.02 (1H, br,), 7.1–7.5 (4H, m,).

EXAMPLE 14 cis-4b,5,9b,10-Tetrahydro-2-methoxy-1,3-dimethylindeno[1,2-b]indole 5,10-Dihydro-2-methoxy-1,3-dimethylindeno[1,2-b]indole (1 g, 3.80 mmol) was stirred at room temperature in glacial acetic acid (15 cm$^3$). Sodium cyanoborohydride (0.75 g, 3 equivalents) was added portionwise over 15 minutes, and the reaction stirred for a further two hours. The reaction was poured into ice/water (30 cm$^3$), and stirred for a further 30 minutes. The solution was neutralised with aqueous sodium hydroxide, and extracted into diethyl ether. The organic extracts were copiously washed with water until the washings were free of cyanide ion. The solvent was removed in vacuo to give the title compound. This was purified by column chromatography to a colourless solid. Yield: 0.8 g (79%). M.p. 117° C. from EtOAc/petrol (60°–80° C.). Elementary analysis: Found: C 81.6, H 7.3, N 5.8, C$_{18}$H$_{19}$NO Calc. for C 81.5, H 7.2, N 5.9, $^1$H NMR (CDCl$_3$) δ: 2.15 (3H, s,), 2.25 (3H, s,), 3.07 (1H, dd,), 3.36 (1H, dd,), 3.64 (3H, s,), 4.1 (1H, br,), 4.19 (1H, ddd,), 5.20 (1H, d,), 6.60 (1H, d,), 6.74 (1H, ddd,), 6.97 (1H, s,), 7.00 (1H, ddd,), 7.17 (1H, d,).

EXAMPLE 15 cis-4b,5,9b,10-Tetrahydro-4b,6,8,9b-tetramethylindeno[1,2-b]indole

A mixture of 5.1 g (0.03 mol) of 2,4-dimethylphenylhydrazine hydrochloride, 5,4 g (0.03 mol) of 2-methyl-1-indanon, 100 ml of ethanol (99, 5%) and 2.5 ml of conc. hydrochloric acid was refluxed for 2 hours. The resulting mixture was filtered, the filtrate was evaporated and the residue partioned between ether and water. The organic phase was washed with aqueous sodium carbonate, dried (MgSO$_4$), filtered and evaporated. The residue was subjected to flash chromatography on 60 Å silica. After elution of non-polar impurities with dichloromethane/isooctane (1/1), a mixture of methanol/ethyl acetate/hexane (1/4/5) eluted 5 g of crude 9b,10-dihydro-6,8,9b-trimethylindeno[1,2-b]indole. Without further purification this material was dissolved in 100 ml of dry tetrahydrofurane. In an argon atmosphere, 50 ml of 1.6M methyl lithium in ether was added at −65° to −55° C. The resulting mixture was kept at −78° C. for 1 hour, and was then poured into a cold aqueous ammonium chloride solution. The mixture was extracted with ether and the combined organic phases were evaporated to yield 5 g of a green oil. Chromatography on 60 Å silica using 7.5% ethyl acetate in isooctane gave 1 g of the title compound. $^1$H NMR (CDCl$_3$) δ; 1.37 (3H,s), 1.48 (3H,s), 2.07 (3H,s), 2.20 (3H, s),3.00–3.35 (2H, AB-system, J 15 Hz), 3.9 (1H,bs) 6.60 (1H,s) 6.88 (1H,s), 7.08–7.28 (4H,m).

EXAMPLE 16 cis-5,5a,6,10b-Tetrahydro-methylindeno[2.1-b]indole

A mixture of 0.6 g (0.00289 mol) of 5,5a, 6,10b-tetrahydroindeno[2,1-b]indole, 0.9 g (0.00723 mol) of K$_2$CO$_3$ and 1.03 g (0.00723 mol) of methyl iodide in 10 ml of acetonitrile was stirred for over the night at room temperature. The resulting mixture was filtered and evaporated. The resulting residue was dissolved in ether and then washed twice with water. Drying (Na$_2$SO$_4$) and evaporation gave 0.25 g (39%) of the title compound. $^1$H NMR (CDCl$_3$) δ, 2.78 (3H, s), 3.2 (2H, d), 4.3 (1H, m) 4.66 (1H, d), 6.37 (1H, d), 6.68(1H, t), 7.06 (1H, t), 7.13–7.18 (2H, m),7.22–7.26 (1H, m) 7.3–7.37 (2H, m).

EXAMPLE 17 cis-4b,5,9b,10-Tetrahydro-8-methoxy-6-methylindeno[1,2-b]indole

To a solution of 5.0 g (0.020 mol) of 5,10-dihydro-8-methoxy-6-methylindeno[1,2-b]indole in 50 ml of tetrahydrofurane was added 8.1 g (0.080 mol) of morpholino borane and dropwise 6.3 ml of conc. hydrochloric acid. The initially exothermic reaction mixture was stirred at room temperature for 72 hour. An additional 6.3 ml of conc. hydrochloric acid was then added and the mixture stirred over night. 25 ml of water was then added and the mixture evaporated. The residue was suspended in 200 ml of water and 5 ml of conc. hydrochloric acid and the mixture was heated on a water bath until most of the solid material had dissolved. The solution was then filtered hot and the filtrate cooled and alkalinized by addition of 10M sodium hydroxide solution. Filtration and washing with water gave 1.93 g (38.4%) of the title compound $^1$H NMR (CDCl$_3$) δ: 2.08 (3H,s), 3.15–3.25 (1H,dd), 3,42–3.55 (1H,dd), 3.7 (3H,s), 4.1–4.22 (1H,t), 5.22–5.28 (1H,d), 6.42–6.46 (1H,d), 6.6–6.65 (1H,d), 7.14–7,25 (3H,m), 7.3–7.4 (1H,m).

EXAMPLE 18 cis-4b,5,9b,10-Tetrahydro-8-methoxy-7,9-dimethylindeno [1.2-b]indole

To an solution of 0.8 g (0.3 mmol) of 5,10-dihydro-8-methoxy-7,9-dimethylindeno[1,2-b]indole and 1,21 g of morpholino borane in 4 ml of dioxane was added dropwise 1 ml of conc. hydrochloric acid. The mixture was refluxed for 30 minutes, then cooled whereupon 3 ml of 6M hydrochloric acid was added. The resulting mixture was then refluxed for 15 minutes. After cooling the solution was alkalinized with aqueous sodium hydroxide and extracted three times with ether. Drying (MgSO$_4$) and evaporation gave a crude product, which was crystallized by dissolving in ethyl acetate and addition of light petroleum at −20° C. Filtration gave 0.73 g (92%) of the title compound. $^1$H NMR(CDCl$_3$) 2.08 (3H,s), 3.15–3.25 (1H,dd), 3,42–3.55 (1H,dd), 3.7 (3H,s), 4.1–4.22 (1H,t) 5.22–5.28 (1H,d), 6.42–6.46 (1H,d), 6.6–6.65 (1H,d) 7.14–7.25 (3H,m), 7.3–7.4 (1H,m).

EXAMPLE 19 cis-4b,5,9b,10-Tetrahydro-6-isopropylindeno[1,2-b]indole

To a solution of 4.95 g (0.020 mol) of 5.10-dihydro-6-isopropylindeno[1,2-b]indole and 8.08 g (0.080 mol) of morpholino borane in 25 ml of dioxane was added dropwise 7 ml of conc. hydrochloric acid. The mixture was refluxed for 30 minutes, cooled to room temperature whereupon 20 ml of 6M hydrochloric acid was added. The mixture was refluxed for 15. After cooling the mixture was alkalinized by addition of aqueous sodium hydroxide and extracted three times with ether. Drying (MgSO$_4$) and evaporation gave a crude product which was purified by column chromatography on silica gel using methylene chloride/light petroleum (20/80) as eluent. Thus 3.53 g (71%) of the title compound was obtained. $^1$H NMR(CDCl$_3$) δ: 1.19 (3H,d), 1.29 (3H, d), 2.84 (1 h,dq), 3,26 (1H,dd), 3.56 (1H,dd), 4,24 (1H,td), 5.31 (1H,d), 6.79 (1H,dd), 6.97 (1H, d), 7.05–7.09 (1H,m), 7,28–7,21 (3H,m), 7.36–7,40 (1H,m).

EXAMPLE 20 cis-4b,5,9b,10-Tetrahydro-4b-methylindeno[1,2-b]inole

A flame-dried flask was charged under an inert atmosphere with 4b,5,9b,10-tetrahydroindeno[1,2-b]indole (1.04 g, 5,02 mmol) and freshly distilled tetrahydrofuran (30 cm$^3$). The solution was cooled to −78° C., and a solution of n-butyllithium (3.45 cm$^3$ of 1.6M solution in hexanes, 1.1 eq) added dropwise. The pale yellow solution was allowed to warm to room temperature, and dry carbon dioxide gas bubbled through, until the solution was colourless. The solvent and excess carbon dioxide were carefully removed at reduced pressure of a vacuum pump, and an atmosphere of dry nitrogen re-introduced. The colourless solid was redissolved in dry tetrahydrofuran (30 cm$^3$), cooled to −78° C., and a further 1.1 equivalents of n-butyllithium added. The reaction was stirred at −78° C. for 1½ hours, and then quenched with iodomethane (0.35 cm$^3$, 1.2 eq). After allowing the reaction to warm to room temperature, the solvents were removed as before, and 2M HCl solution (20 cm$^3$) added. After gas evolution had ceased (ca 20 minutes), the solution was neutralise with solid sodium carbonate. The organic material was extracted into ethyl acetate, and the extract was washed with brine, and dried (Na$_2$SO$_4$). After removal of solvent the product was purified by flash chromatography[R$_F$=0.4(10%-EtOAc/60°–80° C. petrol)] eluting with 5% ethyl acetate/60°–80° C. petrol) as a colourless oil which solidified at −20° C. to give a pink solid. Yield 0.76 g, 69% M.p 52° C.; $^1$H NMR (CDCl$_3$) δ: 7.3–7.1 (5H,m); 6.96(1H,ddd); 6.70(1H,ddd); 6.53(1H,d,J=7.7 Hz), 4.2 (1H, br),3.37 (1H,dm,J=8.2 Hz), 3.48 (1H,dd,J=16.3, 7.2 Hz), 3.14 (1H,dd,J=16.3, 2.0 Hz), 1.61 (3H,s).

EXAMPLE 21 cis-4b,5,9b,10-Tetrahydro-4b-methyl-8-isopropylindeno[1, 2-b]indole

Under an inert atmosphere, a flame-dried flash was charged with 4b,5,9b,10-tetrahydro-8-isopropylindeno[1,2-b]indole (1.49 g 5.98 mmol) and dry tetrahydrofuran (THF, 20 cm$^3$). The solution was cooled to −78° C., and a solution of n-butyllithium in hexanes (4.0 cm$^3$ of 1.6M solution) added dropwise. The reaction was warmed to room temperature, and dry CO$_2$ gas bubbled through until the colour of the anion had dispersed. The solvent and excess CO$_2$ were carefully removed at a vacuum pump, the resulting solid re-dissolved in dry THF (20 cm$^3$) and cooled to −78° C. A further equivalent of n-butyllithium was added, and the reaction stirred at −20° C. for 30 minutes. Iodomethane (0.4 cm$^3$, 1 eq) was added at −78° C., and the reaction warmed to room temperature and stirred for 3 hours. The solvents were removed at the water pump, and 2N HCl solution (20 cm$^3$) added. After 20 minutes, the solution was basified with solid sodium carbonate, and extracted into ethyl acetate. The organic extract was washed with brine, dried (Na$_2$SO$_4$) and concentrated in vacuo. The product was purified by flash chromatography as an unstable pale yellow oil. Yield: 1.01 g, 64%. $^1$H NMR (CDCl$_3$) δ: 7.30–7.15 (4H, m), 7.00 (1H, s), 6.85 (1H, d, J=7.9 Hz), 6.49 (1H, d, J=7.9 Hz), 4.0 (1H, br), 3.73 (1H, d, J=8.1 Hz), 3.49 (1H, dd, J=16.1, 8.2 Hz), 3.16 (1H, d, J=16.1 Hz), 2.79 (1H, septet, J=6.8 Hz), 1.61 (3H, s), 1.19 (6H, d, J=6.8 Hz).

EXAMPLE 22 cis-4b,5,9b,10-Tetrahydro-2-hydroxy-1,3-dimethylindeno [1,2-b]indole.

Under anhydrous conditions, 4b,5,9b,10-tetrahydro-2-methoxy-1,3-dimethylindeno[1,2-b]indole (76 mg, 0.29 mmol) was dissolved in dry dichloromethane (DCM, 1 cm$^3$) into which a small amount of ethanol had been added. The solution was cooled to −78° C., and a solution of boron tribromide in DCM (0.5 cm$^3$ of 1M solution) added. The reaction was slowly warmed to room temperature, reaction occurring at 0° C. After 30 minutes at 10° C., water (1 cm$^3$) was added cautiously, and the reaction stirred for 15 minutes. The mostly solid material was exhaustively extracted between DCM and a saturated solution of sodium bicarbonate. The DCM layer was dried (Na$_2$SO$_4$), and filtered through a pad of flash silica to yield a colourless solid. Yield: 73 mg, 100% .M.p. 178°–180° (dec). $^1$H NMR (CDCl$_3$) δ: 7.16 (1H, d, J =7.3 Hz), 6.99 (1H, ddm), 6.94 (1H, s), 6.73 (1H, ddm, J=7.3, 1.1 Hz), 6.60 (1H, d, J=7.7 Hz), 5.20 (1H, d, J=8.4 Hz), 4.4 (2H, br), 4.15 (1H, ddm), 3.38 (1H, dd, J=16.1, 8.3 Hz), 3.09 (1H, dd, J=16.2 Hz), 2.21 (3H, s), 2.12 (3H, s).

EXAMPLE 23 cis-5-Acetyl-4b,5,9b,10-tetrahydro-2-methoxy-,3-dimethylindeno[1,2-b]indole.

4b,5,9b,10-Tetrahydro-2-methoxy-1,3-dimethylindeno[1,2-b]indole (140 mg, 0.53 mmol) was stirred in acetic anhydride (2 cm$^3$) for 5 minutes. Water (5 cm$^3$) was then added, and stirring continued for 30 minutes. The solution was neutralised with solid sodium bicarbonate, and extracted into dichloromethane. The organic material was dried (MgSO$_4$), concentrated and excess dichloromethane azeotroped on a rotary evaporator using 60°–80° petrol to yield a colourless solid. Yield: 170 mg, 100% .M.p. 201° C. $^1$H NMR (CDCl$_3$) δ: (mixture of E/Z isomers). 8.10 (½H, d, J=7.9 Hz), 8/4–7.0 (4½H, m), 6.24 and 5.75 (1H, d, J=8.2 and 7.7 Hz), 4.23 and 4.13 (1H, ddd, J=7.5 and 8.3 Hz), 3.64 (3H, s), 3.4 (1H, m), 3.13 (1H, 2×dd, J=15.5 Hz), 2.59 and 2.50 (3H, s), 2.53 and 2.22 (3H, s), 2.16 and 2.14 (3H, s).

EXAMPLE 24 cis-5-Acetyl-4b,5,9b,10-tetrahydro-2-hydroxy-1,3-dimethylindeno-[1,2-b]indole.

Under anhydrous conditions a solution of 5-acetyl-4b,5,9b,10-tetrahydro- 2-methoxy-3,3-dimethylindeno[1,2-b]indole (109 mg, 0.35 mmol) in dichloromethane (1 cm$^3$) was cooled to −78° C., and a solution of boron tribromide in dichloromethane (0.7 cm$^3$ of 1M solution) added. The reaction was allowed to warm to room temperature, and stirred for 90 minutes, where-upon water (5 cm$^3$) was cautiously added. After stirring for a further 10 minutes, the mixture was diluted, and extracted with dichloromethane. The combined dichloromethane extracts were dried (Na$_2$SO$_4$) and filtered through a pad of "flash" silica eluting further with 30% EtOAc/60°–80° petrol. Removal of solvent yielded a colourless solid. Yield: 96 mg, 94%. M.p. 205° C. (dec). $^1$H NMR (CDCl$_3$) δ: [mixture of E/Z isomers] 8.06 (½H, d, J=7.1 Hz), 8.05–7.00 (4½H, m), 4.23 and 5.75 (1H, d, J=8.1 and 7.5 Hz), 4.6 (1H, br), 4.22–4.08 (1H,2×ddd), 3.45–3.26 (1H, m), 3.25–3.05 (1H, 2×dd), 2.63 and 2.52 (3H, s), 2.20 and 2.17 (3H, s), 2.13 and 2.11 (3H, s).

EXAMPLE 25 cis 4b,5,9b,10-Tetrahydro-2-methoxy-1,3-dimethyl-8-isopropylindeno[1,2-b]indole.

5,10-Dihydro-2-methoxy-1,3-dimethyl-8-isopropylindeno[1,2-b]indole (1.68 g, 5.5 mmol) was dissolved in trifluoroacetic acid (10 cm$^3$) and stirred vigorously. Triethylsilane (1 cm$^3$, 1.1 eq) was added, and stirring continued for 4 hours. The reaction was poured into water, stirred for 15 minutes, and neutralised with 2M NaOH. All organic material was extracted into ethyl acetate, washed with water and dried (Na$_2$SO$_4$). After removal of solvent, the solid material was recrystallised from 60°–80° petroleum ether as white needles. Yield: 1.18 g, 70% .M.p. 106° C. $^1$H NMR (CDCl$_3$) δ: 7.05 (1H, s), 6.97 (1H, s), 6.88 (1H, dd, J=8.6 Hz), 6.55 (1H, d, J=8.1 Hz), 5.19 (1H, d, J=8.4 Hz), 4.18 (1H, ddd), 3.8 (1H, br), 3.64 (3H, s), 3.36 (1H, dd, J=16.5, 8.3 Hz), 3.07 (1H, d(br) J=16.5 Hz), 2.81 (1H, septet, J=7.0 Hz), 2.25 (3H, s), 2.15 (3H, s), 1.20 (6H, d, J=7.0 Hz).

EXAMPLE 26 cis-4b,5,9b,10-Tetrahydro-2-hydroxy-3-dimethyl-8-isopropylindeno[1,2-b]indole.

A solution of 4b,5,9b,10-tetrahydro-2-methoxy-1,3-dimethyl-8-isopropylindeno[1,2-b]indole (97 mg, 0.32 mmol) in dichloromethane (DCM, 1 cm$^3$) to which some ethanol vapour had been added, was cooled to −78° C. Boron tribromide (0.4 cm$^3$ of 1M solution in DCM) was added, and the reaction warmed to room temperature. Water (1 cm$^3$) was cautiously added, and the mixture partitioned between DCM and sodium bicarbonate solution. The organic layer was dried (Na$_2$SO$_4$) and filtered through a pad of flash silica, eluting with DCM. Removal of solvent yielded a white solid. Yield: 88 mg, 94% M.p. 165° C. (dec.). $^1$H NMR (CDCl$_3$) δ: 7.04 (1H, s) 6.95 (1H, s), 6.87 (1H, dd), 6.56 (1H, d, J=8.1 Hz), 5.20 (1H, d, J=8.6 Hz), 4.16 (1H, ddm), 4.6–4.0 (2H, br), 3.36 (1H, dd), 3.06 (1H, dd), 2.81 (1H, septet, J =7.0 Hz), 2.20 (3H, s), 2.12 (3H, s), 1.19 (6H, d, J=7.9 Hz).

EXAMPLE 27 cis-4b,5,9b,10-Tetrahydro-2,8-dimethoxy-1,3-dimethylindeno[1,2-b]indole.

5,10-Dihydro-2,8-dimethoxy-1,3-dimethylindeno[1,2-b]indole (1.04 g, 3.55 mmol) was dissolved in trifluoroacetic acid (5 cm$^3$) and triethylsilane (0.6 cm$^3$) added with vigorous stirring. Stirring was continued for 4 hours, and the reaction worked up incomplete due to the appearance by t.l.c. of impurities. The solution was poured into water, stirred, and brought to pH 7.0 with solid sodium bicarbonate. The organic material was extracted into DCM, which was washed with sodium bicarbonate solution, and filtered through phase separating filter paper. The product and starting material were separated by column chromatography eluting with 20% EtOAc/60°–80° petrol to yield starting indole (0.06 g, 6%) and a colourless solid. Yield: 0.57 g, 58% .M.p. 149–50° C. (from EtOAc/petrol). $^1$H NMR (CDCl$_3$) δ: 6.99 (1H, s), 6.79 (1H, m), 6.57 (2H, m), 5.18 (1H, d, J=8.5 Hz), 4.18 (1H, dd(br)), 3.74 (3H, s), 3.65 (3H, s), 3.35 (1H, dd, $^3$J=8.4 Hz), 3.06 (1H, d(d)), 2.25 (3H, s), 2.15 (3H, s).

EXAMPLE 28 cis-5-Acetyl-4b,5,9b,10-Tetrahydro-4b,9b-dimethylindeno[1,2-b]indole.

4b,5,9b,10-tetrahydro-4b,9b-dimethylindeno[1,2-b]indole, (0.2 g, 0.85 mmol) was dissolved in acetic anhydride (1 cm$^3$) and the solution stirred at room temperature for 16 hours. The reaction mixture was poured into saturated sodium bicarbonate solution and stirred for a further ½ hour. The mixture was then extracted with ether (3×15 cm³) and the combined organic extracts collected washed with brine, dried (Na$_2$SO$_4$) and evaporated to yield the title compound as an oil. This was purified by flash chromatography on silica gel eluting with 5–7% ethyl acetate/60°–80° petrol, to yield a colourless solid. Yield: 0.15 g, 64% .M.p. 81° C. $^1$H NMR (CDCl$_3$) δ: 7.82 (1H, s), 6.99–7.29 (7H, m), 3.26 (1H, d, J=15.9 Hz), 2.97 (1H, d, J =15.9 Hz), 2.42 (3H, s), 1.77 (3H, s), 1.25 (3H, s).

EXAMPLE 29 cis-4b,5,9b,10-Tetrahydro-4b,8,9b-trimethylindeno[1,2-b]indole

To a solution of 9b,10-dihydro-8,9b-dimethylindeno[1,2-b]indole, (5.05 g, 0.022 mol) in dry tetrahydrofuran (100 cm³) at –78° C., under nitrogen, in a flame dried flask, was added dropwise methyllithium, (1.4M solution in diethyl ether, 23.2 cm³, 0.032 mol). The mixture was stirred at –78° C. for 2 hours and then at –15° C. for a further 1 hour. Saturated ammonium chloride solution (3 cm ) was then added and the mixture allowed to warm to room temperature. The reaction mixture was portioned between ether and saturated ammonium chloride solution and the layers separated. The aqueous phase was extracted with diethyl ether (2×25 cm³) and the combined organic extracts were washed with brine, dried (Na$_2$SO$_4$) and evaporated to afford the title compound as an off white solid. This was purified by flash chromatography on silica gel eluting with 3–10% ethyl acetate/60°–80° petrol to yield a colourless solid. Yield: 2.73 g, 51% .M.p. 208°–212° C. $^1$H NMR (CDCl$_3$) δ: 7.1–7.3 (4H, m), 6.94 (1H, m), 6.77 (1H, d, J=7.8 Hz), 6.46 (1H, d, J=7.8 Hz), 3.35 (1H, d, J=15.9 Hz), 3.06 (1H, d, J=15.9 Hz), 2.22 (3H, s), 1.46 (3H, s), 1.34 (3H, s).

EXAMPLE 30 cis-4b,5,9b,10-Tetrahydro-4b,9b-dimethyl-8-isopropylindeno[1,2-b]indole.

To a solution of methyllithium (1.4M in ether, 14.5 cm³, 12.4 mmol) in dry tetrahydrofuran (20 cm³), at –78° C., under nitrogen, in a flame dried flask, was added dropwise, over 1 hour, a solution of 9b,10-dihydro-9b-methyl-8-isopropylindeno-[1,2-b]indole (1.62 g, 6.20 mmol) in dry tetrahydrofuran (30 cm³). After addition, the mixture was stirred for a further ½ hour at –78° C. Saturated ammonium chloride solution (2 cm³) was then added and the mixture allowed to warm to room temperature. The reaction mixture was then portioned between diethyl ether (50 cm³) and saturated ammonium chloride solution (25 cm³), and the layers separated. The aqueous phase was extracted with diethyl ether (2×10 cm³) and the combined organic extracts were washed brine, dried (Na$_2$SO$_4$) and evaporated. The crude material thus obtained was purified by flash chromatography on silica gel eluting with 3–10% ethyl acetate/60°–80° petrol to yield a pale yellow gum. Yield: 0.77 g, 45%. $^1$H NMR (CDCl$_3$) δ: 7.1–7.3 (4H, m), 6.98 (1H, d, J=1.8 Hz ), 6.82 ( 1H, dd, J=1.8 Hz and 7.9 Hz ), 6.47 (1H, d, J=7.9 Hz), 3.36 (1H, d, J=15.9 Hz), 3.06 (1H, d, J=15.9 Hz), 2.78 (1H, sept., J=6.8 Hz), 1.45 (3H, s), 1.34 (3H, s), 1.18 (6H, dd, J=1.3 Hz and 6.9 Hz).

EXAMPLE 31 cis-5-Acetyl-4b,5,9b,10-tetrahydro-4b,8,9b-trimethylindeno[1,2-b]indole.

4b,5,9b,10-Tetrahydro-4b,8,9b-trimethylindeno[1,2-b]indole (0.25 g, 1.00 mmol) was dissolved in acetic anhydride (1 cm³) and stirred at room temperature for 16 hours. The reaction mixture was poured into saturated sodium bicarbonate solution (25 cm³) and stirred for ½ hour. The mixture was extracted with diethyl ether (3×10 cm³) and the combined organic extracts were washed with brine, dried (Na$_2$SO$_4$) and evaporated. The crude material was purified by flash chromatography on silica gel eluting with 4% ethyl acetate/60°–80° petrol to yield a pale yellow gum. Yield: 0.15 g, 53%. $^1$H NMR (CDCl$_3$) δ: 7.84 (1H, s), 6.90–7.23 (6H, m), 3.26 (1H, d, J=15.9 Hz), 2.96 (1H, d, J =15.9 Hz), 2.40 (3H, s), 2.31 (3H, s), 1.77 (3H, s), 1.32 (3H, s).

EXAMPLE 32 cis-5-Acetyl-4b,5,9b,10-tetrahydro,4b,9b-dimethyl-8-isopropylindeno[1,2-b]indole.

4b,5,9b,10-Tetrahydro-4b,9b-dimethyl-8-isopropylindeno[1,2-b]indole (0.24 g, 0.87 mmol) was dissolved in acetic anhydride (1 cm³) and stirred at room temperature for 16 hours. The reaction mixture was poured into saturated sodium bicarbonate solution (25 cm³) and stirred for ½ hour. The mixture was extracted with ether (3×25 cm³). Combined organic extracts were washed with brine, dried (Na$_2$SO$_4$) and evaporated. The crude material was purified by flash chromatography on silica gel eluting with 4% ethyl acetate/60°–80° petrol to yield a pale yellow gum. Yield: 0.25 g, 89%. $^1$H NMR (CDCl$_3$) δ: 7.84 ((1H, s), 6.90–7.24 (6 h, m), 3.27 (1H, d, J=15.9 Hz), 2.97 (1H, d, J=15.9 Hz), 2.88 (1H, sept., J=6.8 Hz), 2.40 (3H, s), 1.77 (3H, s), 1.33 (3H, s), 1.23 (6H, dd, J=0.73 Hz and 6.8 Hz).

EXAMPLE 33 cis-4b,5,9b,10-tetrahydro-5-ethyl-indeno[1,2-b]indole 5,10-Dihydroindeno[1,2-b]indole (60.0 g, 0.29M) was vigorously stirred in glacial acetic acid (1000 cm³) and to it was added sodium cyanoborohydride (79 g, 1.25M) portionwise over 40 minutes. After 3 hours stirring the reaction mixture was poured onto ice-water (2000 cm³) and the gelatinous solid which formed was separated and stirred with a mixture of ethyl acetate (75 cm³) and water (100 cm³). A colourless solid remained this was found to be unreacted starting material (19.0 g). The original filtrate was extracted with ethyl acetate (2×75 cm³) and the combined organic phases dried and evaporated. The residue was then partly dissolved in a mixture of 60°–80° C. petroleum ether (20 cm³) and ethyl acetate (40 cm³). The residual solid was removed and shown to be impure starting material (2.5 g). The filtrate was extracted with 2M hydrochloric acid (8×25 cm³) and the combined acid extracts were washed with ethyl acetate (2×15 cm³), prior to basification with 0.89 ammonia. The oil which separated was extracted into ethyl acetate (6×25 cm³) and the combined organic layers were then dried and evaporated to give the title compound as a colourless oil. Yield: 34 g, 75%. $^1$H NMR (CDCl$_3$) δ: 1.20 (3H, t, J=7.0 Hz), 3.05 (1H, dd, J=16.5 and 5.0 Hz), 3.38 (2H, q, J=7.0 Hz), 3.40 (1, dd, J=16.5 and 9.0 Hz), 4.12 (1H, ddd, J=9.0, 5.0 and 5.0 Hz), 5.11 (1H, d, J=9.0 Hz), 6.33 (1H, d, J=7.0 Hz), 6.57 (1H, dt, J=7.5 and 1.0 Hz), 7.02 (1H, t, J=8.0 Hz ), 7.08 (1H, d, J=8.0 Hz), 7.14–7.20 (3H, m), 7.34–7.40 (1H, m).

EXAMPLE 34 cis-4b,5,9b,10-Tetrahydro-2-(N,N-Diethylamino)-indeno[1,2-b]indole.

5,10-Dihydro-2-(N,N-diethylamino)-indeno[1,2-b]indole (180 mg, 0.65 mM) was dissolved in trifluoroacetic acid (3 cm³) containing triethylsilane (0.5 cm³) and the solution was stirred at room temperature for 3 hours. It was then treated with water (15 cm³) and 0.89 ammonia (5 cm³), and stirred for a further 0.5 hour. The mixture was extracted with dichloromethane (3×5 cm³), and the combined extracts were filtered through phase separation paper and evaporated to give a pale yellow oil (280 mg). The oil was subjected to column chromatography (silica gel; 7.5% EtAc in 60°–80° petrol ether) giving the title compound as colourless needles. Yield: 65 mg, 35% M.p. 116°–118° C. This product was recrystallized from diethyl ether—60°–80° C. petroleum ether as long colourless needles. M.p. 118° C.; ¹H NMR (CDCl₃) δ: 1.08 (6H, t, J=7.0 Hz), 3.10 (1H, dd, J=16.0 and 2.0 Hz), 3.25 (4H, q, J=7.0 Hz), 3.42 (1H, dd, J=16.0 and 8.5 Hz), 3.55 (1H, br.s), 4.10 (1H, ddd, J=8.5, 8.5 and 2.0 Hz), 5.13 (1H, d, J=8.5 Hz), 6.46 (1H, d, J=2.0 Hz), 6.50–6.60 (2H, m), 6.70 (1H, ddd, J=7.0, 7.0 and 1.0 Hz), 6.95 (1H, ddd, J=7.0, 7.0 and 1.0 Hz), 7.06–7.13 (2H, m).

EXAMPLE 35 cis-(E)- and (Z)-4b,5,9b,10-Tetrahydro-5-acetyl-8-(N,N-diethylamino)-indeno[1,2-b]indole.

(E)- and (Z)-4b,5,9b,10-Tetrahydro-5-acetyl-8-amino-indeno-[1,2-b]indole (1.0 g) sodium carbonate (1 g) and ethyl iodide (2.0 cm³) were heated together at reflux in a mixture of tetrahydrofuran (80 cm³) and water (15 cm³), with stirring, for 24 hours. More ethyl iodide (0.5 cm³) was then added and the heating continued for a further 3 hours. The solvents evaporated and dichloromethane added to the residue. Solids were removed by filtration and these were then washed thoroughly with diethyl ether. Filtrate and washings were combined and reduced in volume to about 15 cm³. On cooling, the title compounds separated out as pale yellow prisms. Yield: 0.75 g, 62% M.p. 176°–178° C.; ¹H NMR (CDCl₃) δ: 1.10 (6H, t, J=7.0 Hz), 1.13 (6H, t, J=7.0 Hz), 2.43 (3H, s), 2.54 (3H, s), 3.21 (1H, d, J=16 Hz), 3.29 (10H, m), 4.06 (1H, dd, J=J=8 Hz), 4.16 (1H, dd, J=J=7.5 Hz), 5.56 (1H, d, J=2 Hz), 5.72 (1H, d, J=7.5 Hz), 6.27 (1H, d, J=8 Hz), 6.47 (2H, ddd, J=7.5, J=2 Hz), 6.63 (1H, d, J=2 Hz), 6.90 (1H, d, J=9 Hz), 7.15–7.23 (6H, m), 7.41 (1H, m), 7.60 (1H, m), 7.89 (1H, d, J=9 Hz).

EXAMPLE 36 cis-4b,5,9b,10-Tetrahydro-5-ethyl-8-(N,N-diethylamino)indeno[1,2-b]indole.

cis-(E)- and (Z)-4b,5,9b,10-Tetrahydro-5-acetyl-8-(N,N-diethylamino)-indeno[1,2-b]indoles (0.32 g, 1 mM) in dry tetrahydrofuran (60 cm³) were treated with lithium aluminium hydride (0.38 g, 10 mM) in portions over a period of 30 minutes. The reaction mixture was then heated at reflux for 3 hours and then excess reagent was destroyed by the addition of 30% sodium ammonium tartrate. The organic solvent was then decanted off and the residue extracted with tetrahydrofuran (3×10 cm³). Solvent and extracts were combined, dried and evaporated to yield an oil which was absorbed onto silica (1 g) and added to the top off a column of silica (5 g), prior to elution with 10 ethyl acetate in 60°–80° C. petroleum ether. The colour of the column became dark blue but the title compound was eluted off as a colour-less oil. Yield: 0.2 g, 65%. The compound is unstable in air becoming blue and then dark red. ¹H NMR (CDCl₃) δ: 1.09 (6H, t, J=7.0 Hz), 1.27 (3H, t, J=7.0 Hz), 3.1–3.3 (5H, m), 3.3–3.5 (3H, m), 4.18 (1H, br.s), 5.07 (1H, br.s), 6.40 (1H, d, J=7.0 Hz), 6.57 (1H, d, J=7.0 Hz), 6.74 (1H, s), 7.22 (3H, s), 7.43 (1H, m).

EXAMPLE 37 cis-4b,5,9b,10-Tetrahydro-8-tert-butylindeno[1,2-b]indole.

A solution of 5,10-dihydro-8-tert-butylindeno[1,2-b]indole (0.57 g, 2.2 mM) in trifluoroacetic acid (5 cm³) was stirred rapidly, and triethylsilane (0.7 cm³, 2 eq) added in one portion. The reaction was stirred overnight, poured into water (10 cm³) and neutralised by the addition of sodium hydroxide. The product was extracted into diethyl ether (2×5 cm³), and the combined extracts were washed with water, dried (Na₂SO₄) and evaporated to yield a pink solid. This was washed with cold petroleum ether (60°–80° C.), and then crystallised from petrol to yield a colourless solid. Yield: 0.47 g, 81% M.p. 103°–105° C.; ¹H NMR (CDCl₃) δ: 7.4–6.9 (6H, m), 6.58 (1H, d, J=8 Hz), 5.25 (1H, d, J=8.5 Hz), 4.15 (2H, br.m), 3.5 (1H, dd, J=16.0 and 9 Hz), 3.2 (1H, d, J=16 Hz), 1.2 (9H, s).

EXAMPLE 38 cis-4b,5,9b,10-Tetrahydro-5-methyl-8-tert-butylindeno[1,2-b]indole.

A flame dried flask was charged with 4b,5,9b,10-tetrahydro-8-tert-butyl-indeno[1,2-b]indole (309 mg, 1.17 mM), and tetrahydrofuran (2.5 cm³). The solution was cooled to −78° C., and a solution n-butyllithium (0.75 cm of 1.6M solution in hexanes, 1.1 eq.) added dropwise. The reaction mixture was stirred at −78° C. for one hour, and iodomethane (0.1 cm³, 1.3 eq) was then added After allowing the reaction to warm slowly to room temperature, a saturated solution of ammonium chloride was introduced, and the organic material extracted into diethyl ether. The organic phase was washed with brine, and dried (MgSO₄). Evaporation of the solvent yielded a light brown oil, which solidified on cooling as a beige solid. Yield: 311 mg, 96%. M.p. 74° C.; ¹H NMR (CDCl₃) δ: 7.5–7.0 (6H, m), 6.32 (1H, d, J=8.3 Hz), 4.91 (1H, d, J=8.8 Hz), 4.16 (1H, ddd, J=9.0, 8.8 and 5.3 Hz), 3.44 (1H, dd, J=16.3 and 9.1 Hz), 3.10 (1H, dd, J =16.3 and 5.3 Hz), 2.95 (3H, s), 1.29 (9H, s).

EXAMPLE 39 cis-4b,5,9b,10-Tetrahydro-4b-methyl-8-tert-butylindeno[1,2-b]indole.

A flame-dried flask was purged with nitrogen and charged with 4b,5,9b,10-tetrahydro-8-tert-butylindeno[1,2-b]indole (240 mg, 0.91 mM) and freshly distilled tetrahydrofuran (3 cm³). The solution so formed was cooled to −78° C., and n-butyllithium (0.60 cm³ of 1.6M solution in hexanes, 1.1 eq.) added dropwise. The pale yellow solution was allowed to warm to room temperature, and dry carbon dioxide gas was bubbled through the solution until it became virtually colourless. The solvent was carefully removed at reduced pressure and an atmosphere of dry nitrogen introduced. The colourless residue was redissolved in dry tetrahydrofuran (3 cm³), and the solution cooled to −78° C., and 1.1 equivalents of n-butyllithium added. The reaction mixture was stirred at −78° C. for 2 hours, and then treated with iodomethane (0.06 cm³), 1.1 eq.). After allowing the reaction to warm to room temperature,the solvents were removed and 2M HCl solution (20 cm³) added. When the gas evolution had ceased (ca 20 minutes), the solution was neutralised with solid sodium carbonate. The organic material was extracted in dichloromethane (3×5 cm³), and the combined extracts were washed with brine, and dried (Na₂SO₄). After removal of solvent, the solid product remaining was purified by flash chromatography [$R_F$=0.4 (10% EtOAc/60°–80° C. petrol)] eluting with 10% ethyl acetate/60°–80° C. petrol. This afforded a pale yellow oil which solidified at −20° C. as a waxy solid. Yield: 0.86 mg, 34%. M.p. 82°–84° C. $^1$H NMR (CDCl$_3$) δ: 7.4–7.0 (6H, m), 6.49 (1H, d, J=9.0 Hz), 4.15 (1H, br.m), 3.71 (1H, br.m), 3.51 (1H, dd, J=16.0 and 9.0 Hz), 3.17 (1H, dd, J=16.0 and 5 Hz), 1.61 (3H, s), 1.27 (9H, s).

EXAMPLE 40 cis-4b,5,9b,10-Tetrahydro-8-fluoroindeno[1,2-b]indole.

A solution of 5-10-dihydro-8-fluoro-indeno[1,2-b]indole (0.8 g, 3.6 mM) in trifluoroacetic acid (5 cm$^3$) was stirred rapidly, and triethylsilane (0.86 cm$^3$, 1.5 eq.) added in one portion. The reaction was stirred for 4 hours and the excess trifluoroacetic acid removed in vacuo. Water (10 cm$^3$) was added to the solid, and the suspension neutralised by the addition of sodium hydroxide. The product was extracted into diethyl ether, which was washed with water, dried and evaporated to yield an off white solid. This was crystallised from ethyl acetate/petroleum ether (60°–80° C.) to yield a colourless solid. Yield: 0.53 g, 81% M.p. 92°–94° C. $^1$H NMR (CDCl$_3$) δ: 7.34 (1H, m), 7.8–7.2 (3H, m), 6.87 (1H, m), 6.69 (1H, m), 6.52 (1H, dd, J=8.4 and 4.4 Hz), 5.27 (1H, d, J=8.8 Hz), 4.16 (1H, ddm, J=8.8 and 8.3 Hz), 4.1 (1H, br.s), 3.51 (1H, dd, J=16.5 and 8.3 Hz), 3.18 (1H, dd, J=16.5 and 2.0 Hz).

EXAMPLE 41 cis-4b,5,9b,10-Tetrahydro-3,7-dinitroindeno[1,2-b]indole.

A solution of cis-4b,5,9b,10-tetrahydroindeno[1,2-b]indole (1.0 g, 4.8 mM) in concentrated sulphuric acid (20 cm$^3$) under vigorous stirring during 45 minutes then cooled to 0° C. and treated with potassium nitrate (0.7 g, 6.9 mM) in small portions over a period of 15 minutes. The cherry red solution was stirred at 0° C. for a further 15 minutes and then poured onto ice. The yellow solid which had formed was collected by filtration and washed firstly with water, and then with hot 25% ethanol-water solution (30 cm$^3$). The filtrate from the last washing was allowed to cool whereupon the title compound separated out as deep yellow platelets. Yield: 0.45 g, 31.5% M.p. 174°–176° C. $^1$H NMR (CDCl$_3$) δ: 3.30 (1H, dd, J=17.5 and 1.0 Hz), 3.65 (1H, dd, J=17.5 and 8.5 Hz), 4.20 (1H, br.s), 4.33 (1H, t, J=8.5 Hz), 5.41 (1H, d, J=8.5 Hz), 7.22 (1H, dd, J=8.0 and 1.0 Hz), 7.28 (1H, d, J=2.0 Hz), 7.38 (1H, d, J=8.5 Hz), 7.50 (1H, dd, J=8.0 and 2.0 Hz), 8.17 (1H, dd, J=8.5 and 2.0 Hz), 8.40 (1H, d, J=2.0 Hz).

EXAMPLE 42 cis-4b, 5,9b,10-Tetrahydro-5-acetyl-3,7-dinitroindeno[1,2-b]indole.

cis-4b,5,9b,10-Tetrahydro-3,7-dinitroindeno[1,2-b]indole (0.40 g, 1.35 mM) and acetic anhydride (1.5 cm$^3$) were heated at 90° C. for 1 hour, cooled and poured into water (7 cm$^3$) ice and the mixture was stirred for 30 minutes. The colourless solid which deposited was collected and taken up into hot ethanol. The after hot filtration, the title compound separated from the cold filtrate as prisms. Yield: 0.42 g, 92% M.p. 264°–266° C.

EXAMPLE 43 cis-(E) and (Z)-4b,5,9b,10-Tetrahydro-5-acetyl-3,7-diaminoindeno[1,2-b]indole.

cis-4b,5,9b,10-Tetrahydro-5-acetyl-3,7-dinitroindeno[1,2-b]indole (0.4 g, 1.2 mM) was stirred in a solution of glacial acetic acid (30 cm$^3$) and water (5 cm$^3$). To this mixture was added titanium trichloride (3 cm$^3$ of a 30% solution in aqueous 24% hydrochloric acid) over a period of 5 minutes. After a further 2 hours, the reaction mixture became colourless and a further portion (0.5 cm$^3$ of the titanium trichloride reagent was introduced. Unreacted staring material was filtered off (0.13 g) and the filtrate was poured onto crushed ice. The pH of the solution thus formed was adjusted to 6 (15 cm$^3$, 0.89 ammonia), and the product extracted into ethyl acetate (8×50 cm$^3$). This extraction was extremely slow because of the formation of emulsions, and was accomplished during 3 days. The extracts were combined and evaporated to give a greenish solid which was triturated with diethyl ether to afford colourless micro prisms. Yield: 0.13 g, 58% M.p. 254°–256° C.

EXAMPLE 44 cis-4b,5,9b,10-Tetrahydro-5-acetyl-3,7-di(-N,N-diethylamino)indeno-[1,2-b]indole.

cis-4b,5,9b,10-Tetrahydro-5-acetyl-3,7-diamino-indeno[1,2-b]indole (0.13 g) was dissolved in tetrahydrofuran (18 cm$^3$) containing water (3.5 cm$^3$), sodium carbonate (0.3 g), and ethyl iodide (0.8 cm$^3$) and heated under reflux for 24 hours. A further quantity of ethyl iodide (0.8 cm$^3$) was then added, and the heating continued for 4 hours. The solvents and excess reagent were removed and the residue extracted with diethyl ether (6×10 cm$^3$). The combined extracts were evaporated to yield a brown gum (0.33 g), this was purified by column chromatography on silica (4 g), eluting with 20% ethyl acetate in 60°–80° C. petroleum ether. This gave the title compound as colourless prisms. Yield: 0.023 g. 12.5% M.p. 137°–138° C. $^1$H NMR (CDCl$_3$) δ: 4×[1.12 (6H, t, J=7.0 Hz)], 2.50 and 2.57 2×[3H, s)], 3.05 (1H, d, J=16.5 Hz), 3.10 (1H, d, J=16.0 Hz), 3.26 and 3.30 4×[(4H, q, J=7.0 Hz)], 3.98 (1H, dd, J=7.5 and 7.5 Hz), 4.07 (1H, dd, J=7.5 and 7.0 Hz), 5.70 (1, d, J =7.5 Hz), 6.23 (1H, d, J=7.0 Hz), 6.32–6.40 (2H, m), 6.59 (2H, ddd, J=8.0, 8.0, 1.5 Hz), 6.96 (2H, d, J=1.0 Hz), 6.95–7.10 (5H, m), 7.61 (1H, d, J=1.5 Hz).

EXAMPLE 45 cis-5,5a,6,10b-Tetrahydro-9-methoxyindeno[2,1-b]indole 5,6-Dihydro-9-methoxyindeno[2,1-b]indole (0.56 g), as a suspension in glacial acetic acid (25 cm$^3$) at 16° C., was treated with sodium cyanoborohydride (1.0 g) in small portions over 6 hours. The resulting solution was stirred for a further 1 hour, and then poured into ice-water (100 cm$^3$). The solution was separated from a small amount of resinous material and the filtrate treated with sodium carbonate (2.5 g) in small portions with vigorous stirring. The colourless solid which separated was collected and crystallised form ethanol as needles. Yield: 0.31 g, 55% M.p. 129°–130° C. $^1$H NMR (CDCl$_3$) δ: 3.06 (1H, dd, J=16.5 and 1.5 Hz), 3.2–3.8 (1H, br.s), 3.31 (1H, dd, J=16.5 and 6.0 Hz), 3.76 (3H, s), 4.71 (1H, d, J=8.0 Hz), 4.80 (1H, ddd, J=8.0, 6.0 and 2.0 Hz), 6.5 (1H, d, J=8.5 Hz), 6.58 (1H, dd, J=8.5 and 2.5 Hz), 6.99 (1H, d, J=2.5 Hz), 7.15–7.24 (3H, m), 7.33–7.36 (1H, m).

EXAMPLE 46 cis,5,5a,6,10b-Tetrahydro-9-isopropylindeno[2,1-b]indole and cis-5,5a,6,10b-Tetrahydro-6-ethyl-9-isopropylindeno[2,1-b]-indole.

To a suspension of 5,6-dihydro-9-isopropylindeno[2,1-b]indole (2.3 g, 9.3 mmol) in glacial acetic acid (30 cm$^3$) was added sodium cyanoborohydride (2 g) in small portions over 30 minutes. The mixture was stirred for 3 hours, and the solution then obtained was poured into ice/water (50 cm$^3$) and stirred for 1 hour. The clear solution was carefully neutralised with sodium hydroxide causing a white precipitate to form. This was extracted into diethyl ether (3×10 cm$^3$), and the combined extracts were washed copiously with water, dried (Na$_2$SO$_4$) and evaporated. Tlc analysis of the residue indicated two products had formed these were isolated by column chromatography eluting with 10% ethyl acetate/petroleum ether (60°–80° C.) to yield first a small amount of cis-5,5a,6,10b-tetrahydro-6-ethyl-9-isopropylindeno[2,1-b]indole (0.07, 3%), and then the title product (0.93 g, 40%), both as colourless oils). Further purification of the last products was achieved by distillation. $^1$H NMR (CDCl$_3$) δ: 7.4–7.1 (5H, m), 6.87 (1H, dd, J=8.1, 1.8 Hz), 6.50 (1H, d, J=8.1 Hz), 4.81 (1H, ddd, J=8.1, 6.2 and 2.0 Hz), 4.73 (1H, d, J=8.1 Hz), 3.32 (1H, dd, J=16.6 and 6.2), 3.08 (1H, dd, J=16.6 and 2.0 Hz ), 2.83 (1H, septet, J=6.9 Hz ), 1.23 (6H, d, 6.9 Hz ).

EXAMPLE 47 cis-5,5a,6,10b-Tetrahydro-9-fluoroindeno[2,1-b]indole.

5,6-Dihydro-9-fluoroindeno[2,1-b]indole (0.55 g, 2.5 mM) in glacial acetic acid (25 cm$^3$) was stirred and treated with sodium cyanoborohydride (2.1 g, 36.5 mM) in small portions over 10 hours, maintaining the temperature below 18° C. The amount of the reducing agent appears crucial since mixtures form if more is added. The reaction mixture was then added to ice-water (100 cm$^3$) and the yellow oil which was formed was separated from the aqueous phase. The pH of the aqueous phase was then adjusted to 6 by the addition of sodium carbonate (30 g), and the colourless oil which was liberated was extracted into diethyl ether (4×20 cm$^3$). The combined extracts were dried and evaporated to yield an oil which was extracted with hot 60°–80° C. petroleum ether (6×10 cm$^3$) and the residue triturated with ethanol (1 cm$^3$). This treatment caused the compound to crystallise as a colourless prisms which recrystallised from ethanol to give the title compound. Yield: 60 mg, 11% M.p. 116°–117° C.; $^1$H NMR (CDCl$_3$) δ: 3.06 (1H, dd, J=16.5 and 1.5 Hz), 3.31 (1H, dd, J=16.5 and 6.0 Hz), 3.67 (1H, br.s), 4.70 (1H, d, J=8.0 Hz), 4.82 (1H, ddd, J=8.0, 6.0 and 1.5 Hz), 6.43 (1H, dd, J=8.5 and 4.0 Hz), 6.70 (1H, ddd, J=8.5, 8.5 and 2.5 Hz), 7.07 (1H, dd, J=8.5 and 2.5 Hz), 7.16–7.25 (3H, m), 7.33 (1H, m).

EXAMPLE 48 cis-9-tert-Butyl-5,5a,6,10b,tetrahydroindeno[2,1,-b]indole

9-Tert-butyl-5,6-dihydroindeno[2,1-b]indole (0.16 mg, 0.6 mM) in glacial acetic acid (25 cm$^3$) was stirred and treated with sodium cyanoborohydride (0.7 g, 11 mM) in small portions over 3 hours, maintaining the temperature below 18° C. The reaction mixture was then added to ice-water (80 cm$^3$) and the yellow oil which was formed was separated from the aqueous phase. The pH of the aqueous phase was then adjusted to 6 by the addition of sodium carbonate (25 g), and the colourless oil which was liberated was extracted into diethyl ether (6×10 cm$^3$). The combined extracts were dried and evaporated to yield an oil which was chromatographed on silica eluting with 5% ethyl acetate in 60°–80° C. petroleum ether. This gave the title compound as colourless prisms. Yield: 0.11 g, 7% M.p. 92° C.; $^1$H NMR (CDCl$_3$) δ: 1.30 (9H, s), 3.05 (1H, d, J=16.5 Hz), 3.28 (1H, dd, J=16.5 and 6.0 Hz), 3.79 (1H, s), 4.70 (1H, d, J=8.0 Hz), 4.75 (1H, ddd, J=8.0, 6.0 and 2.0 Hz), 6.48 (1H, d, J=8.0 Hz), 7.03 (1H, dd, J=8.0 and 2.0 Hz), 7.14–7.24 (3H, m), 7.34 (1H, m), 7.40 (1H, d, J=2.0 Hz).

EXAMPLE 49

9b,10-Dihydro-9b-methylindeno[1,2-b]indole

A flame dried flask was charged with a solution of the phenylhydrazone of 2-methyl-1-indanone (1.47 g, 6.22 mmol) in DCM (30 cm$^3$), followed by phosphorus trichloride (3.4 cm$^3$ of 2.0M solution in DCM). The solution was heated to reflux for 2 hours, cooled, and poured into a saturated solution of sodium hydrogen carbonate. After stirring for 1 hour, the organic material was extracted with more DCM. The basic components were back-extracted into 2M hydrochloric acid. This aqueous solution was made basic, and re-extracted with DCM. Evaporation of the solvent in vacuo, and column chromatography of the residue (20% EtOAc/petrol [60°–80° C.]), gave a clear gum (R$_f$ [10% EtOAc/petrol] 0.1) which could be further purified by bulb to bulb distillation to give the title compound as a gum. Yield: 0.4 g (30%). B.p. 170° C. (0.2 mmHg). $^1$H NMR (CDCl$_3$ δ: 1.39 (3H, s,), 2.84 (1H, d,), 3.11 (1H, d,), 6.4, 8.4 (8H, m,).

EXAMPLE 50 cis-9b,10-Dihydro-8,9b-dimethylindeno[1,2-b]indole

To a solution of 4-methylphenylhydrazine hydrochloride, (9.73 g, 0.06 mmol) in a absolute ethanol (240 cm$^3$) was added dropwise 2-methyl-1-indanone, (8.14 g, 0.056 mmol), followed by conc. hydrochloric acid (3 cm$^3$). The mixture was boiled for 2 hours, the solvents removed, and the residue portioned between diethyl ether and water, and the layers separated. The aqueous phase was extracted with diethyl ether (3×50 cm$^3$). The combined organic phases were washed sequentially with saturated sodium bicarbonate solution and brine, dried (Na$_2$SO$_4$), and evaporated. The crude material thus obtained was purified by flash chromatography on silica gel, eluting with 7–12% ethyl acetate/ 60°–80° petrol to yield a solid (5.05 g, 39%) $^1$H NMR (CDCl$_3$) δ: 7.87 (1H, m) 7.51 (1H, d, J=7.9 Hz) 7.39 (3H, m) 7.25 (1H, s) 7.15 (1H, d, J=8.0 Hz) 3.07 (1H, d, J=14.7 Hz) 2.81 (1H, d, J=14.7 Hz) 2.41 (3H, s) 7.37 (3H, s).

EXAMPLE 51

9b,10-Dihydro-9b-methyl-8-isopropylindeno[1,2-b]indole

To a solution of 4-isopropylphenylhydrazine hydrochloride, (6.50 g, 0.035 mmol) in absolute ethanol (140 cm$^3$) was added dropwise 2-methyl-1-indanone, (4.6 g, 0.032 mmol) followed by conc. hydrochloric acid (2.5 cm$^3$). The mixture was refluxed for 2 hours and the ethanol evaporated. The residue was portioned between diethyl ether (100 cm$^3$) and water (100 cm$^3$) and the layers separated. The aqueous phase was extracted with diethyl ether (2×30 cm$^3$) and the organic extracts were washed sequentially with saturated sodium bicarbonate solution and brine, and then dried (Na$_2$SO$_4$). Removal of the solvent gave the title compound which was purified by flash chromatography on silica gel eluting with 10% ethyl acetate/60°–80° petrol, to yield a yellow gum; (1.62 g, 25%); $^1$H NMR (CDCl$_3$) δ: 7.88 (1H, m), 7.55 (1H, d, J=8.1 Hz) 7.41 (3H, m) 7.30 (1H, d, J=1.8 Hz) 7.23 (1H, dd, J=1.8 Hz and 7.1 Hz) 3.10 (1H, d, J=14.7 Hz) 2.98 (1H, septet, J=7.0 Hz) 2.85 (1H, d, J=14.7 Hz) 1.39 (3H, s) 1.30 (6H, d, J=7.0 Hz).

The starting materials DHII and iso-DHII derivatives are further illustrated by the working examples in our application, EP-A-0 404 536.

EXAMPLE 52 cis-(E)- and (Z)-5-Acetyl-8-amino-4b,5,9b,10-tetrahydroindeno[1,2-b]indole (E)- and (Z)-5-Acetyl-8-nitro-4b,5,9b,10-tetrahydroindeno[1,2-b]indole (4.2 g) in glacial acetic acid (250 cm$^3$) and water (25 cm$^3$) were stirred and treated with 30% aqueous titanium trichloride (42 cm$^3$) over a period of 5 min. After a further 15 min., the reaction mixture was poured on to ice and water (800 cm$^3$) and the pH of the solution adjusted to 4.5 with ammonium hydroxide. The product was then extracted as rapidly as possible into dichloromethane (6×75 cm$^3$). The combined extracts were dried and evaporated to give a solid which was triturated with diethyl ether to afford the title compounds as a colourless solid. Yield: 2.9 g, 77%. M.p. 196°–198° C.; $^1$H NMR δ: 2.42(3H,s), 2.55(3H,), 3.16(1H,d,J=16 Hz), 3.22 (1H,d,J=16 Hz), 3.45(2H,m), 3.65(4H, exchanged by D$_2$O), 4.01(1H,dd,J=8 Hz ), 4.13(1H,dd,J=7.5 Hz), 5.72(1H,d,), 6.26(1H,d,J=8 Hz), 6.46(2H,d,J=8.5 Hz), 6.57(1H,s), 6.64(1H,), 6.82(1H,d,J= 8.5 Hz ), 7.16–7.25(6H,m), 7.38(1H,d,J=7.5 Hz), 7.64(1H, d,J=7.5 Hz ), 7.85(1H,d,J=8.5 Hz). The title compounds can be obtained in similar yield by catalytic hydrogenation of the mixed isomeric nitro compounds over 10% palladium on carbon catalyst using chloroform as the solvent.

EXAMPLE 53 cis-(E)- and (Z)-5-Acetyl-8-(N-acetylamino)-4b,5,9b,10tetrahydroindeno[1,2-b]indole The mixture of cis-(E)- and (Z)-5-Acetyl-8-amino4b,5, 9b,10-tetrahydroindeno[1,2-b]indole from Example 52 were acetylated by conventional methods to give the title compounds. [Found: 74.1;H,5.8;N,9.0C$_{19}$H$_{18}$N$_2$O$_2$ requires: C,74.5;H,5.9;N,9.2%].

EXAMPLE 54 cis-4b,5,9b,10-tetrahydro-4b,6,7,9,9b-pentamethyl-8-methoxyindeno[1,2-b]indole i) 2,3,6-trimethylanisole A mixture of 50 g (0.367 mol) of 2,3,6-trimethylphenol, 55 g (0.4 mol) of potassium carbonate and 36 ml (0.38 mol) of dimethylsulphate in 500 ml of acetonitrile was heated under reflux overnight. 35 ml of conc. aqueous ammonia was then added, and the mixture refluxed for 1 hour. After filtration and evaporation, the residue was taken up in ether and washed twice with NaOH-solution and twice with NaHCO$_3$-solution. Drying (MgSO$_4$) and evaporation gave 50.8 g (92%) of the product.

ii) 4-nitro-2,3,6-trimethylanisole

To a stirred, heated (70°–80° C.) solution of 20.3 g (0.135 mol) of 2,3,6-trimethylanisole in 200 ml of acetic acid was added dropwise 9.65 ml of conc. aqueous HNO$_3$ in 20 ml of acetic acid. After the addition the mixture was poured onto ice, and the resulting mixture was extracted 3 times with methylene chloride. The organic phase was evaporated to remove acetic acid and methylene chloride, and the residue was dissolved in ether and washed twice with NaOH-solution and twice with NaHCO$_3$-solution. Drying (MgSO$_4$) and evaporation gave 19.0 g (72%) of the product, which was used without further purification in the next step.

iii) 4-amino-2,3,6-trimethylanisole

A mixture of 19.0 g (0.097 mol) of 4-nitro-2,3,6-trimethylanisole and 2 small spoons of Pd/C (5%) in 200 of ethanol was hydrogenated for 4 hours in a Parr apparatus. The catalyst was then removed by filtration and the solvent evaporated. The intensive reddish residue was dissolved in ether and extracted with aqueous HCl (2M).

The combined aqueous phases were then alkalinized with NaOH-solution to pH 14. The resulting basic solution was extracted with ether. After drying (MgSO$_4$), the product was precipitated as its HCl-salt by addition of a solution of HCl (g) in ether. Filtration gave 10.1 g (63%) of the product.

iv) 4-hydrazino-2,3,6-trimethylanisole

A suspension of 5.17 g (0.0256 mol) of 4-amino-2,3,6-trimethylanisole hydrochloride in 30 ml of conc. aqueous HCl and 35 ml of water was heated (80° C.) until the hydrochloride dissolved. Cooling to −5° C. resulted in a reprecipitation of the hydrochloride as small fine crystals. To this stirred mixture 1.77 g (0.0256 mol) of NaNO$_2$ in 15 ml of water was added during 30 minutes, while the reaction temperature was kept between −5° C. to 0° C. After stirring at this temperature for 15 minutes further, a solution of 14.46 g (0,064 mol) of SnCl$_2$×2H$_2$O in 12 ml of conc. aqueous HCl was added dropwise during 15 minutes while keeping the temperature at 0° C. The reaction mixture was then allowed slowly to attain room temperature and was then alkalinized with NaOH-solution until pH 14. The resulting mixture was extracted with ether, and after drying (MgSO$_4$) the product was precipitated as its hydrochloride by addition of HCl (g) in ether. Filtration gave 3.8 g (69%) of the product.

v) 9b,10-dihydro-6,7,9,9b-tetramethyl-8-methoxyindeno [1,2-b]indole

A mixture of 2.2 g (0.012 mol) of 4-hydrazino-2,3, 6trimethylanisole, 1.9 g (0.013 mol) of 2-methyl-1-indanone and 2 ml of conc. aqueous HCl in 20 ml of ethanol was refluxed under argon for 1 hour. After cooling the solvent was removed by evaporation and the residue was partitioned in a mixture of water and methylene chloride. The aqueous phase was neutralized by addition of aqueous NaHCO$_3$ and the phases separated. After drying (MgSO$_4$) and evaporation of the organic phase, the remaining crude product was purified by chromatography on silica using methylene chloride as an eluant. This gave 1.1 g 31% of the product which was used directly in the next step.

(v) cis-4b,5,9b,10-tetrahydro-4b,6,7,9,9b-pentamethyl-8-methoxyindeno[1,2-b]indole To a cold (−80° C.) solution of 1.1 g (0.0038 mol) of 9b,10-dihydro-6,7,9,9b-tetramethyl-8-methoxyindeno[1,2-b]indole in 20 ml of dry THF was added 4 ml of 1.6M methyl lithium in ether under argon. The mixture was stirred at −78° C. for 1 hour and then at −20° C. for 1 hour. After attaining 0° C. aqueous NH$_4$Cl and ether was added. The phases were separated, and the organic phase was washed once with water, dried (MgSO$_4$) and evaporated. The resulting crude product was purified by chromatography on silica using ethyl acetate/isooctane (2/10) as eluant. This gave 0.3 g (25%) of the expected product. $^1$H NMR (CDCl$_3$): 1.41 (3H,s), 1.43 (3H,s), 1.96 (3H,s), 2.07 (3H,s), 2.35 (3H,s), 3.0 (1H,d), 3.55 (3H,s), 3.65 (1H,d), 7.1 (3H,m), 7.25 (1H,m).

EXAMPLE 55 cis-5,5a,6,10b-tetrahydro-7-methyl-9-methoxyindeno[2,1-b]indole i) 4-hydrazino-3-methylanisole A cooled, stirred suspension of 33.0 g (0.19 mol) of 2-methyl-4-methoxyaniline. HCl in 100 ml of 6N hydrochloric acid was treated dropwise, under argon, with a solution of 13.1 g (0.19 mol) of sodium nitrite dissolved in 35 ml of water. The rate of addition was such that the temperature did not exceed +5° C. After the addition was completed, the resulting mixture was stirred for 30 minutes further at the same temperature. The reaction mixture was then added with stirring under argon to a cooled (+5° C.) solution of 101.7 g (0.58 mol) of Na$_2$S$_2$O$_4$ dissolved in 500 ml of water. After stirring for 20 minutes at this temperature, 250 ml of ether was added, followed by alkalinization to pH9 with 10N sodium hydroxide solution. The organic phase was separated and washed with sodium chloride solution. After drying (Na$_2$SO$_4$), treatment with charcoal and filtration, the product was precipitated as the hydrochloride by addition of HCl(g)/ether (to pH3). Filtration and washing with ether and chloroform gave 29.6 g (69%) of the product. M.p. 105° C.

ii) 5,6-dihydro-7-methyl-9-methoxyindeno[2,1-b]indole

A mixture of 1.9 g (0.01 mol) of 4-hydrazino-3-methylanisole hydrochloride and 1.3 g (0.01 mol) of 1-indanone in 25 ml of acetic acid was refluxed under argon for 6 hours. After dilution with water the resulting mixture was extracted 3 times with methylene chloride. The combined organic phases were washed twice with NaOH solution (1M), dried (Na$_2$SO$_4$), treated with charcoal and evaporated giving the crude product. Purification on silica using methylene chloride as eluant gave 0.85 g (34%) of the product. M.p. 208° C.

iii) cis-5a,5,6,10b-tetrahydro-7-methyl-9-methoxyindeno[2,1-b]indole

To a stirred suspension of 0.74 g of (0.00296 mol) of 5,6-dihydro-7-methyl-9-methoxyindeno[2,1-b]indole in 25 ml of acetic acid was added 0.93 g (0.0148 mol) of NaCNBH$_3$ in portions during 5 minutes. The mixture was stirred for 3 hours at room temperature, whereafter it was diluted with water and then stirred for another hour. The resulting mixture was alkalinized with NaOH-solution (10M) to pH9, and was then extracted twice with ether. The combined organic phases were washed twice with aqueous NaCl-solution and dried (Na$_2$SO$_4$). After evaporation the residue was purified by chromatography on silica using methylene chloride as eluant. This gave 0.61 g (24%) of the expected product. M.p. 104° C. $^1$H NMR (CDCl$_3$): 2.2 (3H,s), 3.0–3.4 (2H,dd), 3.4–3.5 (1H,bs), 3.75 (3H,s), 4.65–4.80 (2H,m), 6.4–7.4 (6H,m)—thereof 6.45 (1H,dd), 6.75 (1H,dd).

(iv) The racemic mixture obtained in step iii) was separated and the enantiomers obtained had the following physiochemical properties:

(−)-Cis-5,5a,6,10b-tetrahydro-7-methyl-9-methoxyindeno[2,1-b]indole

[α]$_D$=−14.5° (C=1, CH$_2$Cl$_2$)

Mp. 93.5° C.

(+) Cis-5,5a,6,10b-tetrahydro-7-methyl-9-methoxyindeno[2,1-b]indole

[α]$_D$=+14.5° (C=1, CH$_2$Cl$_2$)

Mp. 93.5° C.

EXAMPLE 56

Cis-4b,5,9b,10-tetrahydro-8-methoxy-4b,6,9b-trimethylindeno[1,2]indole i) 2-methyl-4-methoxyphenylhydrazole of 2-methyl-1-indanone.

A mixture of 14.9 g (0.08 mol) of 4-hydrazino-3-methylanisole (prepared as described in Example 55(i)) and 20 g (0.24 mol) of sodium acetate in 60 ml of water was stirred thoroughly and then filtered. To the stirred filtrate 9.3 g (0.06 mol) of 2-methyl-1-indanone in 10 ml of ethanol was added resulting in the separation of a reddish oil. Upon cooling of the mixture the oil crystallized. The crystals were collected and recrystallized from ethanol giving 5.0 g (30%) of the expected product.

ii) 9b,10-dihydro-8-methoxy-6,9b-dimethylindeno[1,2]indole.

To a stirred solution of the hydrazone obtained above in 100 ml of ethanol 75 ml of HCl-saturated ether was added at 35° C. during 15 minutes. The mixture was heated at 35°–45° C. for 10 minutes and was then allowed to cool. After evaporation of the solvent the residue was dissolved in methylene chloride, washed with dilute sodium chloride (aq), dried (Na$_2$SO$_4$) and evaporated giving 1.7 g (35%) of the crude product as a brown oil. This was used directly in the next step without further purification.

iii) Cis-4b,5,9b,10-tetrahydro-8-methoxy-4b.6.9b-trimethylindeno[1,2]indole

The crude 1.7 g (0,006 mol) material obtained above was dissolved in 20 ml of dry tetrahydrofuran and cooled to −78° C. under argon. To this stirred solution 10 ml of methyllithium (1.6M) in ether was added, whereupon the mixture was allowed to attain room temperature (3 h). Quenching was then achieved by addition of a mixture of ether and saturated ammonium chloride solution. The organic phase was separated, washed with water, dried (Na$_2$SO$_4$) and evaporated. The residue was purified by chromatography on silica gel using ethyl acetate/isocyanate (2/8) as eluant. A final washing with isooctane of the resulting oil gave 0.4 g (24%) of the product as colourless crystals. $^1$HNMR(CDCl$_3$) 1.35 (3H,s), 1.5 (3H,s), 2.1 (3H,s), 3.08 (1H,d), 3.38 (d,1H), 3.7 (3H,s), 6.44 (1H,d), 6.63 (1H,d), 7.1–7.28 (3H,m), 7.35 (1H,d).

EXAMPLE 57

Cis-4b,5,9b,10-tetrahydro-8-ethoxy-4b,7,9,9b-tetramethylindeno[1,2-b]indole.

i) 4-nitro-2,6-dimethyl-1-ethoxybenzene

A mixture of 10 g (0.0598 mol) of 4-nitro-2,6-dimethylphenol, 16.5 g (0.1196 mol) of K$_2$CO$_3$ and 18.6 g (0.1196 mol) of ethyl iodide in 100 ml of acetonitrile was refluxed for 2.5 hours. The solid material was removed by hot filtration and was then washed with hot acetonitrile. The combined organic phase was evaporated and the resulting residue dissolved in ether. The ether phase was washed with water, dried (Na$_2$SO$_4$) and evaporated yielding 11.4 g (98%) of the product, M.p. 56° C.

ii) 3,5-dimethyl-4-ethoxyaniline

A solution of 11.4 g (0,058 mol) of 4-nitro-2,6-methyl-1-ethoxybenzene in 115 ml of ethanol (95%) wash hydrogenated using Pd/C as catalyst overnight. After removal of the catalyst by filtration the solvent was removed by evaporation yielding 9.2 g (96%) of the product, M.p. 74° C.

iii) 3,5-dimethyl-4-ethoxyphenylhydrazine

To a cooled (+5° C.), stirred suspension of 9.2 g (0.0557 mol) of 3,5-dimethyl-4-ethoxyaniline in 50 ml of 6N HCl (aq), 3.8 g (0.0557 mol) of NaNO$_2$ in 15 ml of water was added during 30 minutes. After stirring at +5° C. for 30 minutes further, the resulting mixture was added under argon and stirring to 29.1 g (0.167 mol) of sodium dithionite dissolved in 150 ml of water. After stirring for 20 minutes at +5° C., 250 ml of ether was added followed by alkalinization to pH 9 with 10N sodium hydroxide solution. The organic phase was separated and washed with sodium chloride solution. After drying (Na$_2$SO$_4$) the product was precipitated as the hydrochloride by addition of HCl(g)/ether (to pH 3).

Filtration and washing with ether gave 9.4 g (78%) of the product.

iv) 9b,10-dihydro-8-ethoxy-7,9,9b-trimethylindeno[1,2-b]indole

A solution of 2.16 g (0.01 mol) of 3,5-dimethyl-4-ethoxyphenylhydrazine hydrochloride and 1.46 g (0.01 mol) of 2-methyl-1-indanone in 20 ml of acetic acid was stirred overnight at room temperature and then refluxed for 3 hours. The mixture was diluted with water, alkalinized with 10N sodium hydroxide solution and extracted three times with methylene chloride. The combined organic phase was washed with water, dried ($Na_2SO_4$) and evaporated giving 2.8 g of crude product which was recrystallized from light petroleum/ethyl acetate (5/1). Yield 2.1 g (72%). M.p. 164° C.

v) cis-4b,5,9b,10-tetrahydro-8-ethoxy4b,7,9,9b-tetramethylindeno[1,2-b]indole

To a cold (−78° C.) solution of 2.0 g (0.0063 mol) of 9b,10-dihydro-8-ethoxy-7,9,9b-trimethylindeno[1,2-b]indole in 20 ml of dry tetrahydrofuran, 10 ml of methyllithium (1.6N) in ether was added dropwise with stirring and under argon. After the addition was complete the stirring was continued for 1 hour at −20° C. and then for 1 hour at room temperature. The reaction mixture was quenched by addition of 20 ml of saturated ammonium chloride solution. After addition of 100 ml of ether the organic phase was separated and washed twice with ammonium chloride solution. Drying ($Na_2SO_4$) and evaporation gave 2.0 g (96%) of the product. $^1$H NMR ($CDCl_3$): 1.35 (3H,t), 1.4 (6H,d), 2.1 (3H,s), 2.35 (3H,s), 2.95–3.05 (1H,d), 3.55–3.75 (3H,m), 6.1 (1H,s), 7.0–7.3 (4H,m).

EXAMPLE 58

Cis-4b,5,9b,10-tetrahydro-8-methoxy-6,7,9-trimethylindeno[1,2-b]indole.

i) 5,10-dihydro-8-methoxy-6,7,9-trimethylindeno[1,2-b]indole

A mixture of 1.95 g (0.009 mol) of 4-hydrazino-2,3,6trimethylanisole hydrochloride (prepared as described in Example 54) and 1.06 g (0.008 mol) of 1-indanone in 20 ml of ethanol and 2 ml of concentrated hydrochloric acid was refluxed for 1 hour. The solvent was removed by evaporation and the residue partitioned between ether and water. The aqueous phase was made alkaline with sodium hydroxide solution. The organic phase was separated and washed with water. Drying ($Na_2SO_4$) and evaporation gave the crude product which was purified by chromatography using methylene chloride/light petroleum (20/80) as eluant. A final recrystallization gave 1.08 g (49%) of the product.

ii) cis-4b,5,9b,10-tetrahydro-8-methoxy-6,7,9-trimethylindeno[1,2-b]indole.

To a solution of 0.65 g (0.00234 mol) of 5,10-dihydro-8-methoxy-6,7,9-trimethylindeno[1,2-b]indole and 0.95 g (0.00957 mol) of morpholino borane in 4 ml of dioxane was added dropwise 1 ml of concentrated hydrochloric acid. The mixture was refluxed for 30 minutes, cooled to room temperature whereupon 3 ml of 6N hydrochloric acid was added. The mixture was then refluxed for another 30 minutes. After cooling to room temperature, the crude mixture was partitioned between ether and aqueous sodium hydroxide. The organic phase was separated and washed with aqueous sodium hydroxide and with water. Drying ($MgSO_4$) and evaporation gave the crude product which was recrystallized from ethyl acetate/light petroleum. Yield 0.46 g (70%). $^1$H NMR ($CDCl_3$): 2.0 (3H,s), 2.14 (3H,s), 2.28 (3H,s), 3.17 (1H,dd), 3.55 (1H,dd), 3.64 (1H,s), 4.28 (1H, ddd), 5.38 (1H,d), 7.20–7.27 (3H,m), 7.39 (1H,d).

EXAMPLE 59

Cis-4b,5,9b,10-tetrahydro-4,6-dimethyl-8-methoxyindeno[1.2b]indole i) 4-Hydrazino-3-methylanisole hydrochloride 33 g (0.19 mol) 4-methoxy-2-methylaniline hydrochloride was suspended in 100 ml (6M) hydrochloric acid under argon atmosphere. The mixture was cooled to +5° C. and a solution of 13.1 g (0.19 mol) $NaNO_2$ in 35 ml water was added dropwise at such rate that the temperature was kept below +5° C. After the addition was completed the solution was stirred for 30 min at +5° C. 101.7 g (0.58 mol) $Na_2S_2O_4$ was dissolved in 500 ml wager at +5° C. and the solution was poured into the reaction mixture and stirred for 30 min. 250 ml diethyl ether was added and made basic with NaOH (10M) until pH 9. The phases were separated and the water phase extracted with diethyl ether. The combined organic phases were washed with NaCl(aq) and dried with $Na_2SO_4$. The ether phase was filtered through celite. A saturated solution of HCl(g) in ether was added to the solution containing the product and the hydrochloride salt of the hydrazine precipitated. The crystals were collected on a suction filter and washed with diethyl ether and chloroform. 29.5 g (82%) of the product was isolated.

ii) 5,10-Dihydro-4,6-dimethyl-8-methoxyindeno[1,2b]indole 130 ml ethanol, a saturated solution of HCl(g) in 130 ml ether, 5.8 g (31 mmol) 4-hydrazino-3-methylanisole hydrochloride and 4.8 g (31 mmol) 7-methyl-1-indanone were added to a flask. The solution was stirred at room temperature overnight. Some 7-methyl-1-indanone still remained in the reaction mixture. An excess of the 4-hydrazino-3-methylanisole hydrochloride (0.6 g) was added and the solution was stirred overnight. The solvent was evaporated and the crude dissolved in ether, washed two times with NaOH (1M) and with water. The organic phase was dried with $Na_2SO_4$, filtered and evaporated. The remaining oil was chromatographed and eluated with dichloromethane. 1.3 g (16%) of the product was isolated.

iii) Cis-4b,5,9b,10-tetrahydro-4,6-dimethyl-8-methoxyindeno[1,2-b]indole 16 ml dioxane, 1.3 g (4.9 mmol) 5,10-dihydro-4,6-dimethyl-8-methoxyindeno[1,2-b]indole and 1.98 g (19.6 mmol) morpholineborane were added to a round bottom flask. 4 ml hydrochloric acid (conc.) was added dropwise during stirring of the solution. The reaction mixture was refluxed for 1 hour. 8 ml (6M) hydrochloric acid was added and the solution was refluxed for 30 min. After the solution had reached room temperature, 50 ml water was added. The mixture was made basic with NaOH(aq) until pH 9. The product was extracted with dichloromethane two times. The organic phase was dried with $Na_2SO_4$ and the solvent was evaporated. The product was subjected to chromatography in dichloromethane. The isolated product was dissolved in acetonitrile, a saturated solution of HCl(g) in ether was added and the product precipitated as the hydrochloride salt and was removed by filtration. 1.2 g (82.2%) of product was isolated. $^1$H NMR ($CDCl_3$):2.33 (3H,s), 2.48 (3H, s), 2.95 (1H, dd), 3.56 (1H, dd), 3.77 (3H, s), 4.44 (1H, ddd), 5.71 (1H, d), 6.78 (1H, s), 6.93 (1H, s), 7.11–7.17 (2H, m), 7.30 (1H, d).

Pharmacological Properties

The indenoindoles described in the present invention are hydrophobic and stable structures which form cations, stable cation radicals or radicals upon oxidation. They constitute potent antioxidants as measured by inhibition of $Fe^{2+}$-ascorbate induced lipid peroxidation in vitro, with $IC_{50}$ value as low as 10 nM. The compounds of formulas (IA) and (IB) prevent efficiently oxidation of lipoproteins in human plasma in the presence of rabbit smooth muscle cells or mouse peritoneal macrophages. They also prevent ischemic/reperfusion damage to the isolated perfused rat heart, and protect against carbon tetrachloride-, acetaminophen-, methylmethane sulfonate-, menadione-, t-butyl hydroperoxide-, and N-methyl-$N^1$-nitro-N-nitrosoguanidine-induced liver damage in mice, or in isolated rat hepatocytes.

These properties suggest that the structures of formulas (IA) and (IB) have a potential use in the protection or treatment of ischemic or reperfusion injury, particularly cerebral and cardiac ischemia/infarct, atherosclerosis, thrombosis, embolism, Parkinson's disease, ageing, Alzheimer's disease, neoplasms and toxicity of anti-neoplastic drugs, immunusuppresive agents and inflammation including allergic/inflammatory conditions like broncial asthma and rheumatoid arthritis. Other potential applications are chemoprevention against chemical toxicity or radiation damage. The indenoindole compounds are not appreciably activated by UV light making them candidates for use in skin care products. Another interesting and important feature of the indenoindole compounds of the present invention is their ability to stabilize membranes.

Pharmacological Tests

The most remarkable feature of the compounds of the invention is their efficacy as free-radical scavengers or antioxidants. An assay system measuring the concentration of the compounds of formulas (IA) and (IB) required to inhibit lipid peroxidation by 50% ($IC_{50}$) was used. The lipid peroxidation assay is described below and the data presented in Table 1. Other assays described below are the red blood cell fragility test used for measuring membrane stabilisation by indenoindoles (Table 2), and protection by indenoindoles against cytotoxicity of N-methyl-$N^1$-nitro-N-nitrosoguanidine (MNNG) in rat hepatocytes (Table 3). MNNG is a highly cytotoxic agent, the mechanism of action of which may involve a radical-mediated membrane destabilization. Additionally a test of inhibition of macrophage induced LDL-peroxidation is described below and the data is presented in Table 4.

1. Ascorbate/$Fe^{2+}$-dependent lipid peroxidation

For the ferrous/ascorbate lipid peroxidation system, 6.25 ml of 0.1M potassium phosphate buffer ($KP_i$), pH 7.4, was added to 12.5 mg dried soy bean phospholipids. After flushing with argon for 2 min, the suspension was sealed with five layers of Parafilm and sonicated until the suspension was translucent. The final reaction mixture was composed of 200 µg/ml phospholipid, 10 µM $FeNH_4(SO_4)_2$ or $Fe(NH_4)_2(SO_4)_2$, and 100 µM ascorbic acid in 0.1M $KP_i$ (pH 7.4), and the antioxidant to be tested in acetone or DMSO. The volume of vehicle never exceeded 1% of the total volume. The reaction was initiated by the addition of ascorbic acid plus iron. The reaction was continued at room temperature in a shaking water bath for 30 min and then stopped by the addition of 10 µM of 0.5M butylated hydroxytoluene in DMSO. The above procedure and the subsequent determination of 2-thiobarbituric acid-reactive material is described in: Shertzer, H. G. et al, Biochem. Pharmacol. 37, 333 (1988). Table 1 shows the effects of indenoindoles and α-tocopherol on ascorbate/$Fe^{2+}$-dependent lipid peroxidation.

TABLE 1

| Compounds | $pIC_{50}$ |
| --- | --- |
| 9-Methoxy-7-methyl-iso-THII[(−)cis] | 8.4 |

TABLE 1-continued

| Compounds | $pIC_{50}$ |
| --- | --- |
| 9-Methoxy-7-methyl-iso-THII[(+)cis] | 8.4 |
| 8-Methoxy-4,6-dimethyl-THII | 8.4 |
| 9-Methoxy-7-methyl-iso-THII (racemic) | 8.2 |
| 2,8-Dimethoxy-1,3,dimethyl-THII | 8.1 |
| 8-Methoxy-6,7,9-trimethyl-THII | 8.0 |
| 8-Methoxy-6-methyl-THII | 8.0 |
| 8-Methoxy-4b,6,9b-trimethyl-THII | 8.0 |
| 2-Hydroxy-1,3-dimethyl-THII | 7.9 |
| 8-Ethoxy-4b,7,9,9b-tetramethyl-THII | 7.9 |
| 8-Isopropyl-4b,9b-dimethyl-THII | 7.7 |
| 8-Isopropyl-4b-nethyl-THII | 7.7 |
| 9-Methoxy-iso-THII | 7.7 |
| 4b,8,9b-Trimethyl-THII | 7.6 |
| 8-Methoxy-4b,6,7,9,9b-pentamethyl-THII | 7.6 |
| 8-Fluoro-THII | 7.5 |
| 4b,6,8,9b-Tetramethyl-THII | 7.4 |
| 9-Isopropyl-iso-THII | 7.4 |
| 6,8-Dimethyl-THII | 7.3 |
| 8-Isopropyl-THII | 7.3 |
| 4b,9b-Dimethyl-THII | 7.2 |
| 2-Methoxy-1,3-dimethyl-THII | 7.2 |
| 2-Diethylamino-THII | 7.2 |
| 8-Methyl-THII | 7.1 |
| 4b-Methyl-THII | 7.1 |
| 8-Diethylamino-5-ethyl-THII | 7.1 |
| 8-Methoxy-5-methyl-THII | 7.0 |
| 9b-Methyl-THII | 7.0 |
| THII | 6.9 |
| iso-THII | 6.9 |
| 10,10-Dimethyl-THII | 6.9 |
| 4b,5,8,9b-Tetramethyl-THII | 6.8 |
| 5,8-Dimethyl-THII | 6.4 |
| 6-Methyl-iso-THII | 6.1 |
| 5-Methyl-THII | 6.1 |
| α-Tocopherol (Vitamin E) | 5.0 |

2. Membrane stabilization in red blood cells

The membrane stabilization effect of indenoindoles was assayed by the red blood cell fragility test. Rats were anesthesized with 65 mg pentobarbital per kg body weight by i.p. injection. Blood samples were removed into a heparinized syringe from the left ventricle and diluted 20-fold with buffer containing 140 mM NaCl, 10 mM sodium citrate and 5 mM glucose (pH 7.4) at 0° C. Diluted blood was kept on ice. A 0.75 ml aliquot of blood was added to a 4 ml cuvette containing 10 µl DMSO or 10 µl of the antioxidant dissolved in DMSO vehicle. After 1 min of gentle swirling, 0.75 ml of 0.9 % NaCl or $H_2O$ were added to the cuvette by forceful pipetting, and the absorbance at 656 nm was recorded with a Beckman DU-70 spectrophotometer. When $H_2O$ was added in the absence of a stabilizing agent, absorbance decreased within 15 sec to 0.8. Addition of NaCl instead of $H_2O$ gave a time-independent absorbance of 2.2. In the presence of increasing concentrations of stabilizing chemicals, the absorbance decrease observed after the addition of water was diminished. The % protection from osmolysis was obtained from the equation [E(2.2−0.8)−A/2.2−0.8)]×100%, where A=2.2 minus the absorbance decrease when water is added in the presence of a known concentration of chemical. The % protection is then plotted against several concentrations of the chemical being treated. The red blood cell fragility protective index value (RBC-PIV) is the linear regression slope of this plot, expressed as the percentage protection against osmolysis per µM protecting agent. Table 2 shows the RBC-PIV values for different indenoindoles and a-tocopherol.

TABLE 2

| Compound | RBC-PIV (%/μM) |
|---|---|
| 8-Methoxy-THII | 0.21 |
| iso-THII | 0.38 |
| THII | 0.41 |
| 9-Methyl-THII | 0.48 |
| 5-Methyl-THII | 0.64 |
| α-Tocopherol | 0.10 |

3. Protection against cytotoxic effects of MNNG in hepatocytes

The protective effects of indenoindoles on MNNG-induced cytotoxicity was assayed with rat hepatocytes. Hepatocytes were prepared from male Sprague-Dawley rats by collagenase treatment as originally described by Zahlten and Stratman (Zahlten, R. N. and Stratman, F. W., Arch. Biochem. Biophys. 163, 600 (1988)), as modified by Reitman et al (Reitman, F. A., Shertzer, H. G. and Berger, M. L., Biochem. Pharmacol. 37,3183 (1988)). In order to improve viability, cells were centrifuged through 0.508 g/ml Percoll (Pharmacia AB, Uppsala, Sweden) in 137 mM NaCl, 8.1 mM $Na_2HPO_4$ and 1.5 mM $KH_2PO_4$ (pH 7.4). Putative protecting agents were added to the cells as solutions in DMSO, with the final concentration of DMSO never exceeding 5 μl/ml of cell suspension. MNNG was added to a concentration of 0.5 mM as a solution in ethanol, giving a final concentration of ethanol of 1%; ethanol alone was by itself without effect. Viability was determined as the percentage of cells that excluded 0.2 % trypan blue. The protective effects by indenoindoles and α-tocopheryl-acetate on cytotoxicity are shown in Table 3.

Values are the concentration of compound required to extend by 1 hour the time needed for MNNG to kill 50 % of the viable cells.

TABLE 3

| Compound | $IC_{50}$ (μM) |
|---|---|
| iso-THII | 2.0 |
| THII | 2.2 |
| 5-Methyl-THII | 2.2 |
| α-Tocopheryl-acetate | 161 |

4. Inhibition of macrophage induced LDL-peroxidation

Mouse peritonal macrophages were incubated in Ham's F10 medium in the presence of 25 μg of human low density lipoproteins (LDL)/ml of macrophage medium. The compounds of the invention were dissolved in ethanol and added to a final concentration of $10^{-5}$ to $10^{-10}$M. The cells in triplicate were then incubated for 24 hours. The cell medium was then removed, and the lipid peroxidation was assayed by measuring the formation of thio-barbituric acid reactive substances (TBARS) using a method described by Steinbrecher et al in Proc. Natl. Acad. Sci. USA 81, 3883 (1984). The results are given in Table 4 as the −log of the concentrations necessary to reduce lipid peroxidation by 50% compared to control ($pIC_{50}$).

TABLE 4

| Compounds | $pIC_{50}$ |
|---|---|
| 9-Methoxy-7-methyl-iso-THII (racemic) | 8.7 |
| 2,8-Dimethoxy-1,3-dimethyl-THII | 7.4 |
| 8-Methoxy-6,7,9-trimethyl-THII | 7.9 |
| 8-Methoxy-6-methyl-THII | 8.3 |
| 8-Methoxy-4b,6,9b-trimethyl-THII | 8.6 |
| 2-Hydroxy-1,3-dimethyl-THII | 7.1 |
| 8-Ethoxy-4b,7,9,9b-tetramethyl-THII | 7.8 |
| 8-Isopropyl-4b,9b-dimethyl-THII | 7.4 |
| 8-Isopropyl-4b-methyl-THII | 7.4 |
| 9-Methoxy-iso-THII | 8.0 |
| 8-Fluoro-THII | 6.8 |
| 4b,6,8,9b-Tetramethyl-THII | 7.9 |
| 8-Methoxy-4b,6,7,9,9b-pentamethyl-THII | 7.9 |
| 6,8-Dimethyl-THII | 7.4 |
| 8-Isopropyl-THII | 7.0 |
| 4b,9b-Dimethyl-THII | 7.5 |
| 2-Methoxy-1,3-dimethyl-THII | 7.1 |
| 2-Diethylamino-THII | 7.6 |
| 8-Methyl-THII | 6.9 |
| 4b-Methyl-THII | 7.4 |
| 8-Diethylamino-5-ethyl-THII | 7.6 |
| 9b-Methyl-THII | 7.0 |
| THII | 7.0 |
| iso-THII | 6.7 |
| 10,10-Dimethyl-THII | 7.4 |
| 4b,5,8,9b-Tetramethyl-THII | 7.7 |
| 5,8-Dimethyl-THII | 6.6 |
| 6-Methyl-iso-THII | 6.1 |
| 5-Methyl-THII | 6.6 |

We claim:
1. A compound or its enantiomer of the formula IA or IB

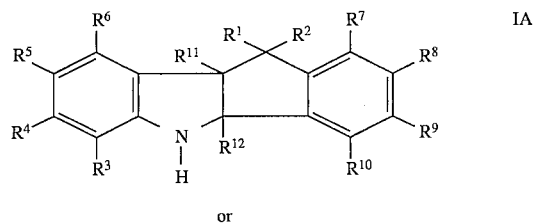

or

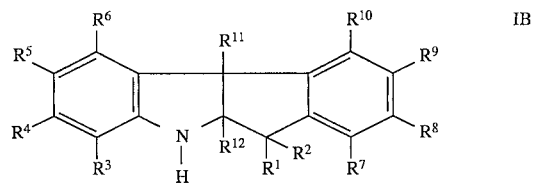

or a pharmaceutically acceptable salt thereof wherein each of $R^1$, $R^2$, $R^3$, $R^4$, $R^6$, $R^7$, $R^8$, $R^9$, $R^{10}$, $R^{11}$ and $R^{12}$ is independently selected from hydrogen or an alkyl group containing 1–6 carbon atoms and $R^5$ is an alkoxy group containing 1–6 carbon atoms.

2. A compound according to claim 1 wherein at least one of $R^3$, $R^7$, $R^9$, $R^{11}$ and $R^{12}$ is methyl, ethyl or i-propyl.

3. A compound according to claim 1 wherein $R^5$ is methoxy.

4. A compound according to claim 1 wherein $R^1$, $R^2$, $R^4$, $R^6$ and $R^{10}$ are hydrogen.

5. A compound according to claim 1 wherein $R^3$, $R^4$, $R^6$, $R^{11}$ and $R^{12}$ are each an alkyl group containing 1–6 carbon atoms and $R^1$, $R^2$, $R^7$, $R^8$, $R^9$ and $R^{10}$ are each hydrogen.

6. A compound according to claim 1 wherein $R^1$, $R^2$, $R^4$, $R^6$, $R^7$, $R^8$, $R^9$ and $R^{10}$ are each hydrogen and $R^3$ is an alkyl group containing 1–6 carbon atoms.

7. A compound according to claim 1 wherein $R^5$ is ethoxy.

8. A compound according to claim 1 of formula IA wherein $R^{11}$ and $R^{12}$ are either both hydrogen or both a lower alkyl group; $R^3$, $R^4$ and $R^6$, which may be the same or different, are hydrogen or an alkyl group containing 1–6 carbon atoms; and $R^1$, $R^2$, $R^7$, $R^8$, $R^9$ and $R^{10}$ are each hydrogen.

9. Cis-5,5a,6,10b-tetrahydro-7-methyl-9-methoxyindeno[2,1-b]indole, an enantiomer or a pharmaceutically acceptable salt thereof.

10. Cis-4b,5,9b,10-tetrahydro-8-methoxy-6-methylindeno[1,2-b]indole, an enantiomer or a pharmaceutically acceptable salt thereof.

11. Cis-4b,5,9b,10-tetrahydro-4b,6,7,9,9b-pentamethyl-8-methoxyindeno[1,2-b]indole, an enantiomer or a pharmaceutically acceptable salt thereof.

12. Cis-4b,5,9b,10-tetrahydro-8-ethoxy-4b,7,9,9b-tetramethyl-indeno[1,2-b]indole, an enantiomer or a pharmaceutically acceptable salt thereof.

13. Cis-4b,5,9b,10-tetrahydro-8-methoxy-6,7,9-trimethylindeno[1,2-b]indole, an enantiomer or a pharmaceutically acceptable salt thereof.

14. Cis-4b,5,9b,10-tetrahydro-4,6-dimethyl-8-methoxyindeno[1,2-b]indole, an enantiomer or a pharmaceutically acceptable salt thereof.

15. Cis-4b,5,9b,10-tetrahydro-8-methoxy-4b,6,9b-trimethylindeno[1,2-b]indole, an enantiomer or a pharmaceutically acceptable salt thereof.

16. A compound, an enantiomer or a pharmaceutically acceptable salt thereof selected from cis-4b,5,9b,10-tetrahydro-8-methoxy-5-methylindeno[1,2-b]indole;

cis-4b,5,9b,10-tetrahydro-8-methoxyindeno[1,2-b]indole;

cis-4b,5,9b,10-tetrahydro-8-methoxy-7,9-dimethylindeno[1,2-b]indole; and cis-5,5a,6,10b-tetrahydro-9-methoxyindeno[2,1-b]indole.

17. A method for treating a medical disorder associated with free radical formation which comprises administering to a patient in need of such treatment an effective amount of a compound or its enantiomer of formula IA or IB

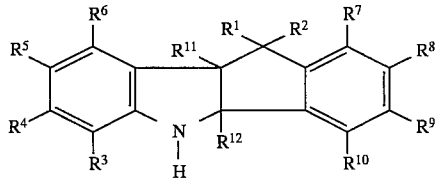

IA or

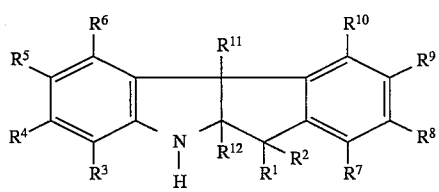

IB or a pharmaceutically acceptable salt thereof wherein each of $R^1$, $R^2$, $R^3$, $R^4$, $R^6$, $R^7$, $R^8$, $R^9$, $R^{10}$, $R^{11}$ and $R^{12}$ is independently selected from hydrogen or an alkyl group containing 1–6 carbon atoms and $R^5$ is an alkoxy group containing 1–6 carbon atoms.

18. A method according to claim 17 wherein the disorder is atherosclerosis.

19. A method according to claim 17 wherein the disorder is ischemic or reperfusion injuries, thrombosis, or embolism.

20. A method according to claim 17 wherein the disorder is a neoplasm.

21. A method for the treatment of atherosclerosis which comprises administering to a patient in need of such treatment an effective amount of cis-4b,5,9b,10-tetrahydro-4b,6,7,9,9b-pentamethyl-8-methoxyindeno[1,2-b]indole, an enantiomer or a pharmaceutically acceptable salt thereof.

22. A method for the treatment of atherosclerosis which comprises administering to a patient in need of such treatment an effective amount of cis-5,5a,6,10b-tetrahydro-7-methyl-9-methoxyindeno[2,1-b]indole, an enantiomer or a pharmaceutically acceptable salt thereof.

23. A method for the treatment of atherosclerosis which comprises administering to a patient in need of such treatment an effective amount of cis-4b,5,9b,10-tetrahydro-8-methoxy-6-methylindeno[1,2-b]indole, an enantiomer or a pharmaceutically acceptable salt thereof.

24. A method for the treatment of atherosclerosis which comprises administering to a patient in need of such treatment an effective amount of cis-4b,5,9b,10-tetrahydro-8-ethoxy-4b,7,9,9b-tetramethylindeno[1,2-b]indole, an enantiomer or a pharmaceutically acceptable salt thereof.

25. A method for the treatment of atherosclerosis which comprises administering to a patient in need of such treatment an effective amount of cis-4b,5,9b,10-tetrahydro-8-methoxy-6,7,9-trimethylindeno[1,2-b]indole, an enantiomer or a pharmaceutically acceptable salt thereof.

26. A method for the treatment of atherosclerosis which comprises administering to a patient in need of such treatment an effective amount of cis-4b,5,9b,10-tetrahydro-4,6-dimethyl-8-methoxyindeno[1,2-b]indole, an enantiomer or a pharmaceutically acceptable salt thereof.

27. A pharmaceutical composition comprising an active ingredient which is a compound as defined in claim 1, an enantiomer or a pharmaceutically acceptable salt thereof and a pharmaceutically acceptable carrier.

* * * * *